(12) United States Patent
Wood et al.

(10) Patent No.: US 11,504,154 B2
(45) Date of Patent: Nov. 22, 2022

(54) TRANSPERINEAL IMAGING-GUIDED PROSTATE NEEDLE PLACEMENT

(71) Applicant: The United States of America, as represented by the Secretary, Department of Health and Human Services, Bethesda, MD (US)

(72) Inventors: Bradford Wood, Potomac, MD (US); Sheng Xu, Rockville, MD (US); Reza Seifabadi, Bethesda, MD (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 677 days.

(21) Appl. No.: 16/320,980

(22) PCT Filed: Jul. 28, 2017

(86) PCT No.: PCT/US2017/044344
§ 371 (c)(1),
(2) Date: Jan. 25, 2019

(87) PCT Pub. No.: WO2018/022979
PCT Pub. Date: Feb. 1, 2018

(65) Prior Publication Data
US 2019/0175214 A1      Jun. 13, 2019

Related U.S. Application Data

(60) Provisional application No. 62/367,923, filed on Jul. 28, 2016.

(51) Int. Cl.
*A61B 17/34*      (2006.01)
*A61B 8/00*      (2006.01)
(Continued)

(52) U.S. Cl.
CPC ........ *A61B 17/3403* (2013.01); *A61B 8/4209* (2013.01); *A61B 8/463* (2013.01);
(Continued)

(58) Field of Classification Search
CPC ... A61B 17/3403; A61B 8/4209; A61B 8/483; A61B 8/5246; A61B 10/0241; A61B 2010/045; A61B 2017/3411
See application file for complete search history.

(56) References Cited

U.S. PATENT DOCUMENTS

| 5,623,931 A * | 4/1997 | Wung ................ A61B 17/3403 600/461 |
| 2003/0153850 A1 * | 8/2003 | Davis .................. A61B 8/4209 601/2 |

(Continued)

FOREIGN PATENT DOCUMENTS

| WO | WO 2010/140075 | 12/2010 |
| WO | WO 2015/008279 | 1/2015 |

OTHER PUBLICATIONS

"Ultrasound-Guided Transperineal Needle Biopsy of the Prostate After Abdominoperineal Resection" by B.D. Fornage et al. J Clin Ultrasound. 23:263-265. May 1995 (Year: 1995).*

(Continued)

*Primary Examiner* — Jason M Ip
(74) *Attorney, Agent, or Firm* — Leydig, Voit and Mayer

(57) ABSTRACT

Prostate biopsy systems are provided that include a 3D ultrasound probe support configured to receive an ultrasound probe for transperineal imaging. One or more template grids can have a plurality of apertures extending therethrough to receive and guide a biopsy needle along a trajectory associated with respective apertures when the template grid is fixed to the support and the biopsy system is positioned in the perineal area of a patient. Patient-specific template grids can also be developed and produced. This system enables (Continued)

fully transperineal prostate biopsy (i.e. both imaging and needle placement are perineal) and eliminates the need for an external racking device for image fusion as well as needle tracking. In addition, it reduces the infection risk associated to transrectal approach.

19 Claims, 31 Drawing Sheets

(51) Int. Cl.
*A61B 8/08* (2006.01)
*A61B 10/02* (2006.01)
*A61B 90/11* (2016.01)
*A61B 34/10* (2016.01)

(52) U.S. Cl.
CPC .............. *A61B 8/466* (2013.01); *A61B 8/483* (2013.01); *A61B 8/5261* (2013.01); *A61B 10/0241* (2013.01); *A61B 90/11* (2016.02); *A61B 8/0841* (2013.01); *A61B 2017/3411* (2013.01); *A61B 2017/3413* (2013.01); *A61B 2034/105* (2016.02); *A61B 2034/107* (2016.02)

(56) References Cited

U.S. PATENT DOCUMENTS

| | | |
|---|---|---|
| 2005/0080333 A1 | 4/2005 | Piron et al. |
| 2009/0118724 A1 | 5/2009 | Zvuloni et al. |
| 2011/0009742 A1* | 1/2011 | Lachaine ............. A61B 8/4227 600/427 |
| 2011/0009748 A1 | 1/2011 | Greene et al. |
| 2014/0276081 A1* | 9/2014 | Tegels ................... A61B 8/085 600/461 |
| 2015/0245825 A1 | 9/2015 | Stone |
| 2015/0366546 A1* | 12/2015 | Kamen ................. A61B 90/11 600/461 |

OTHER PUBLICATIONS

International Search Report, dated Nov. 13, 2017, from PCT Application No. PCT/US2017/044344, 4 pages.
Written Opinion, dated Nov. 13, 2017, from PCT Application No. PCT/US2017/044344, 7 pages.

* cited by examiner

TRANSPERINEAL IMAGING-GUIDED PROSTATE NEEDLE PLACEMENT

CROSS REFERENCE TO RELATED APPLICATIONS

This is the U.S. National Stage of International Application No. PCT/US2017/044344, filed Jul. 28, 2017, which was published in English under PCT Article 21(2), which in turn claims the benefit of U.S. Provisional Application No. 62/367,923, filed Jul. 28, 2016. The provisional application is incorporated herein in its entirety.

FIELD OF THE DISCLOSURE

The present disclosure is directed to systems and methods of guiding prostate needle placement procedures, and more specifically, to utilizing transperineal ultrasound imaging systems for the same.

BACKGROUND

Prostate cancer is the most common male cancer in the United States with an estimated 220,000 new cases and 28,000 deaths in 2015. If cancer or other disorders of the prostate are suspected, a biopsy can be performed to obtain tissue samples from the patient for subsequent laboratory analysis.

Prostate biopsy is typically performed under transrectal ultrasound (TRUS) guidance. TRUS is real-time, relatively low cost, and shows the prostate capsule and boundaries. However, it suffers from poor spatial resolution and low sensitivity for cancer detection. To improve the accuracy of target identification and cancer diagnosis, intraoperative TRUS images can be fused with preoperative MR images. These systems, however, continue to require TRUS imaging which, because of the invasiveness of the procedure, is stressful to patients and can result in increased risk of infections. In addition, in order to achieve this fusion of images, TRUS systems must use tracking devices such as electromagnetic (EM) tracking, which increases the expense and makes the imaging process more cumbersome.

Because of the importance of effective diagnostic imaging of the internal anatomy of the prostate and adjacent areas of the body, improvements in imaging systems and techniques are desirable.

SUMMARY

Methods and systems are disclosed herein for performing biopsies of the prostate, or otherwise guiding needles into the prostate, using transperineal imaging, such as ultrasound, in combination with needle guides and/or template grids fixed relative to ultrasound probe supports. Such systems and methods can provide, for example, improved accuracy and efficiency in prostate cancer diagnosis, make it less invasive, less prone to infection, and eliminate the need for an external tracking device for US-MRI fusion, thanks to use of a 3D ultrasound probe. Inclusions of a 3D ultrasound transducer can enable sensorless (i.e., without external tracking) fusion of US-MRI. Using a transperineal 3D imaging system along with transperineal needle insertion, a fully transperineal prostate biopsy system can be achieved (i.e., both us probe and needle placement are trasnperineal). Further, the process of 3D ultrasound image reconstruction (as a pre-requisite for US-MR registration) can be performed in a "sensorless" manner using an external 3D imaging probe located adjacent the perineum rather than in the rectum. To achieve "sensorless" needle placement, the system can utilize a grid template which is fixed relative to the probe such that the needle trajectories are in a known orientation relative to the 3D image. Different embodiments of the grids allows one to reach the entire prostate, despite the presence of the probe on the perineum (conventionally, an endorectal probe is placed and thus the whole premium is available for needle insertion).

In one embodiment, a prostate biopsy system includes an ultrasound probe support configured to receive a 3D ultrasound probe, one or more template grids (in a known relative position thus enabling sensorless fusion guidance) having a plurality of apertures extending therethrough to receive and guide a biopsy needle along a trajectory associated with respective apertures, and a frame coupled to the ultrasound probe support. The frame can be movable to position the ultrasound probe adjacent a perineal area of a patient to obtain transperineal ultrasound images of the patient. Without a template that is in a known position relative to the imaging probe, and without a 3D imaging probe, one cannot achieve sensorless prostate biopsy.

One or more template grids can be used, including template grids that extend above the ultrasound probe support, extend laterally from the ultrasound support, or both. In addition, the template grids can include a central grid portion and a pair of laterally-extending grid portions.

The template grid(s) can be flat or curved, in which case the grid can define a concave side facing the patient and a convex side facing away from the patient. The template grid(s) can be pivotably coupled to the ultrasound probe support or frame member to allow movement (i.e., pivoting) relative to the ultrasound probe support.

The frame can include a movable stage that allows the ultrasound probe support to move relative to a portion of the frame. In some embodiments, the movable stage can include a linear actuator (manual or motorized) that permits the movable stage to move towards or away from the patient to facilitate positioning of the ultrasound probe relative to the perineal area of the patient.

In another embodiment, a method of performing a biopsy of a prostate of a patient is provided. The method can include coupling an ultrasound probe to an ultrasound probe support that has one or more template grids fixed thereto, with the template grids having a plurality of apertures extending therethrough to receive and guide a biopsy needle along a trajectory associated with respective apertures. The ultrasound probe can be positioned adjacent a perineal area of the patient and an ultrasound image of the prostate can be acquired. The one or more template grid can be registered to the ultrasound images and, if desired, to other preoperative high-resolution images (e.g., MRI scans). The ultrasound image can be displayed (along with the preoperative images) and one or more apertures can be selected based on the intersection of their trajectories with a targeted tissue area of the prostate. A biopsy needle can be inserted into the selected aperture(s) and a biopsy sample of the targeted tissue area of the prostate can be obtained.

In some embodiments, the positioning of the ultrasound probe comprises moving a frame coupled to the ultrasound probe support, such as by actuating a linear actuator (manual or motorized) to move a portion of the frame towards the perineal area of the patient.

The template grids used in the methods can include an upper template grid, one or more laterally-extending grids, a central grid portion, or various combinations of the same.

The grids can be flat or curved, and, in some embodiments, can be moveable (e.g., pivotable) relative to the ultrasound probe support.

A preoperative high-resolution image (e.g., MRI or CAT scan) can be registered with the 3D ultrasound image and displayed along with the ultrasound image, either in an overlapping manner or side-by-side.

In another embodiment, a method of making a patient-specific template grid for use during a biopsy of a patient's prostate is provided. The method can include obtaining a preoperative high-resolution volume scan of the prostate and adjacent areas; segmenting the preoperative high-resolution volume scan to obtain a 3D model of the prostate, pubic arch, and perineum of the patient; and displaying the 3D model patient along with one or more proposed template grid. The one or more template grids can have a plurality of proposed apertures that define respective trajectories through the template grid for guiding a biopsy needle and the proposed template grid can be modified to change the proposed template grid and/or the proposed apertures to alter the respective trajectory of the proposed apertures. Once a final design is chosen, the template grid(s) can be formed, such as by machining, molding, 3D printing, or some combination of the same.

Since the real-time transperineal 3D ultrasound images can be obtained while the position of the ultrasound probe is fixed (e.g., via the frame and/or passive positioning arm) relative to the perineal area of the patient, the registration of preoperative images (e.g., MR images) with real-time ultrasound images can be achieved by a sensorless system (e.g., a sensorless MR-US fusion system). Also, since the grid template is fixed relative to the 3D US probe, the needle placement is also performed sensorless.

The foregoing and other features and advantages of the disclosed technology will become more apparent from the following detailed description of several embodiments which proceeds with reference to the accompanying figures.

DETAILED DESCRIPTION

Figure 1:
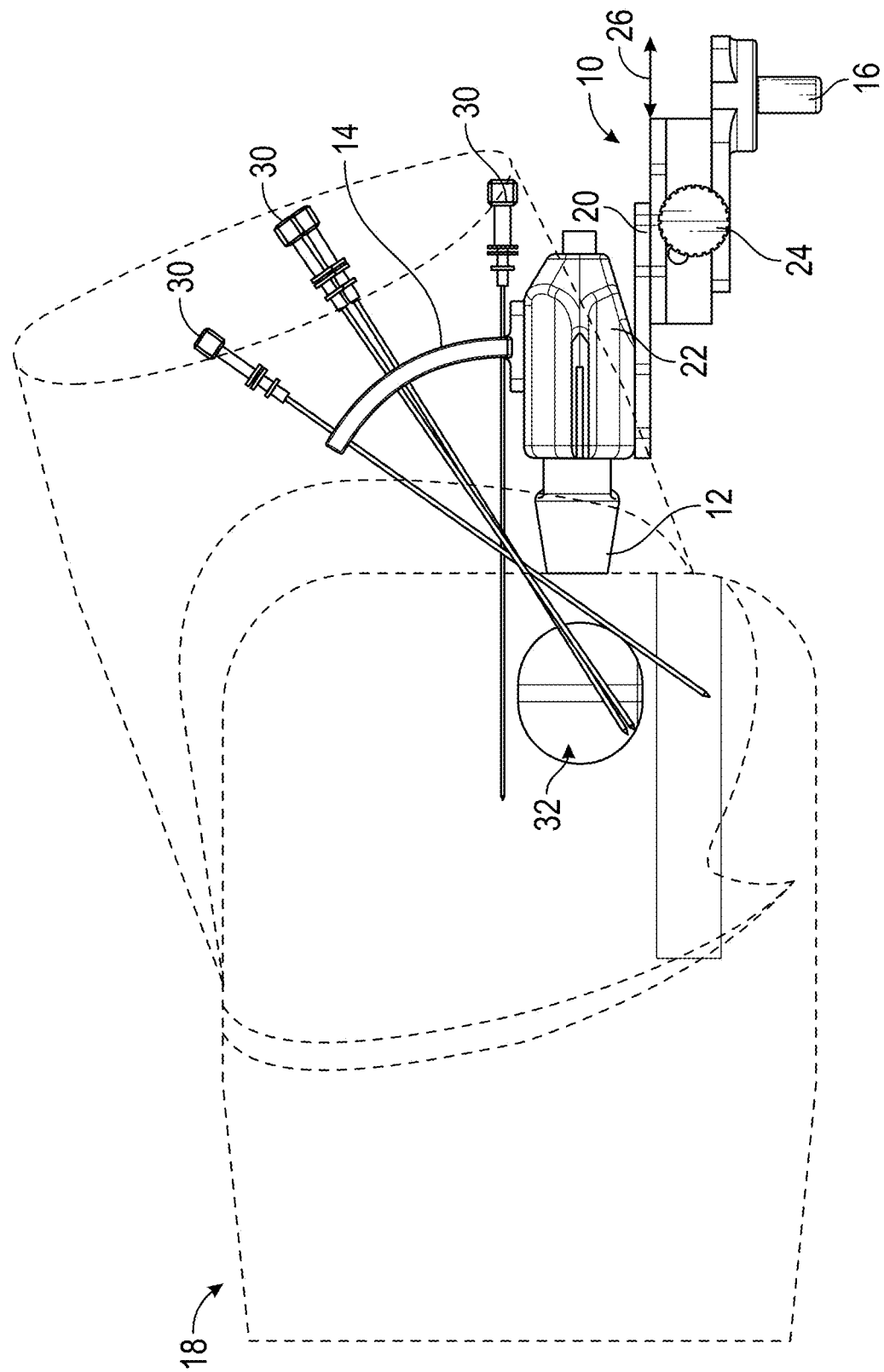
FIG. 1 illustrates a side view of a biopsy system including a frame that supports a 3D ultrasound probe for transperineal positioning and an upwardly-extending template grid for needle guidance.

The following description is exemplary in nature and is not intended to limit the scope, applicability, or configuration of the invention in any way. Various changes to the described embodiment may be made in the function and arrangement of the elements described herein without departing from the scope of the invention.

As used in this application and in the claims, the singular forms "a," "an," and "the" include the plural forms unless the context clearly dictates otherwise. Additionally, the term "includes" means "comprises." Further, the terms "coupled" or "associated" generally mean electrically, electromagnetically, and/or physically (e.g., mechanically or chemically) coupled or linked and does not exclude the presence of intermediate elements between the coupled or associated items absent specific contrary language.

Although the operations of exemplary embodiments of the disclosed method may be described in a particular, sequential order for convenient presentation, it should be understood that disclosed embodiments can encompass an order of operations other than the particular, sequential order disclosed. For example, operations described sequentially may in some cases be rearranged or performed concurrently. Further, descriptions and disclosures provided in association with one particular embodiment are not limited to that embodiment, and may be applied to any embodiment disclosed. In describing different embodiments that have similar features with similar functions, like reference numerals are used.

Moreover, for the sake of simplicity, the attached figures may not show the various ways (readily discernable, based on this disclosure, by one of ordinary skill in the art) in which the disclosed system, method, and apparatus can be used in combination with other systems, methods, and apparatuses. Additionally, the description sometimes uses terms such as "produce" and "provide" to describe the disclosed method. These terms are high-level abstractions of the actual operations that can be performed. The actual operations that correspond to these terms can vary depending on the particular implementation and are, based on this disclosure, readily discernible by one of ordinary skill in the art. As used herein, when used as a term of degree, the term "generally" is used to mean "effectively" or "substantially." In the context of "generally parallel" or "generally perpendicular," for example, "generally" means within ± 15 degrees of parallel or perpendicular, respectively.

FIG. 1 illustrates a side view of a biopsy system including a frame 10 that supports an ultrasound probe 12 for transperineal positioning and a template grid 14 for needle guidance. Template grid can be pre-registered with the ultrasound probe based on its known shape and orientation relative to the ultrasound probe.

Frame 10 can include a coupling member 16 that is configured to be coupled to a passive positioning arm (not shown) that can be readily adjusted to achieve the desired position of the frame relative to a patient 18. Frame 10 can further comprise a moveable stage 20, which can move relative to the positioning arm when frame 10 is coupled to the positioning arm. Moveable stage 20 can be a linear stage actuator (manual or motor-driven) that permits linear movement of an ultrasound probe support 22 (and the probe itself when positioned on the probe support 22) along at least a portion of the frame to achieve a desired position of the ultrasound probe relative to the patient (e.g., positioning the probe to achieve a desired acoustic contact with the perineal area of the patient). The linear stage actuator can comprise a manual adjustment knob 24, which allows for fine adjustments of the location of the moveable stage 20 relative to the patient. Once the ultrasound probe is positioned as desired relative to the patient's perineum, the location of the ultrasound probe can be fixed. This permits sensorless MR-US fusion to be achieved, as discussed further herein.

Figure 2:
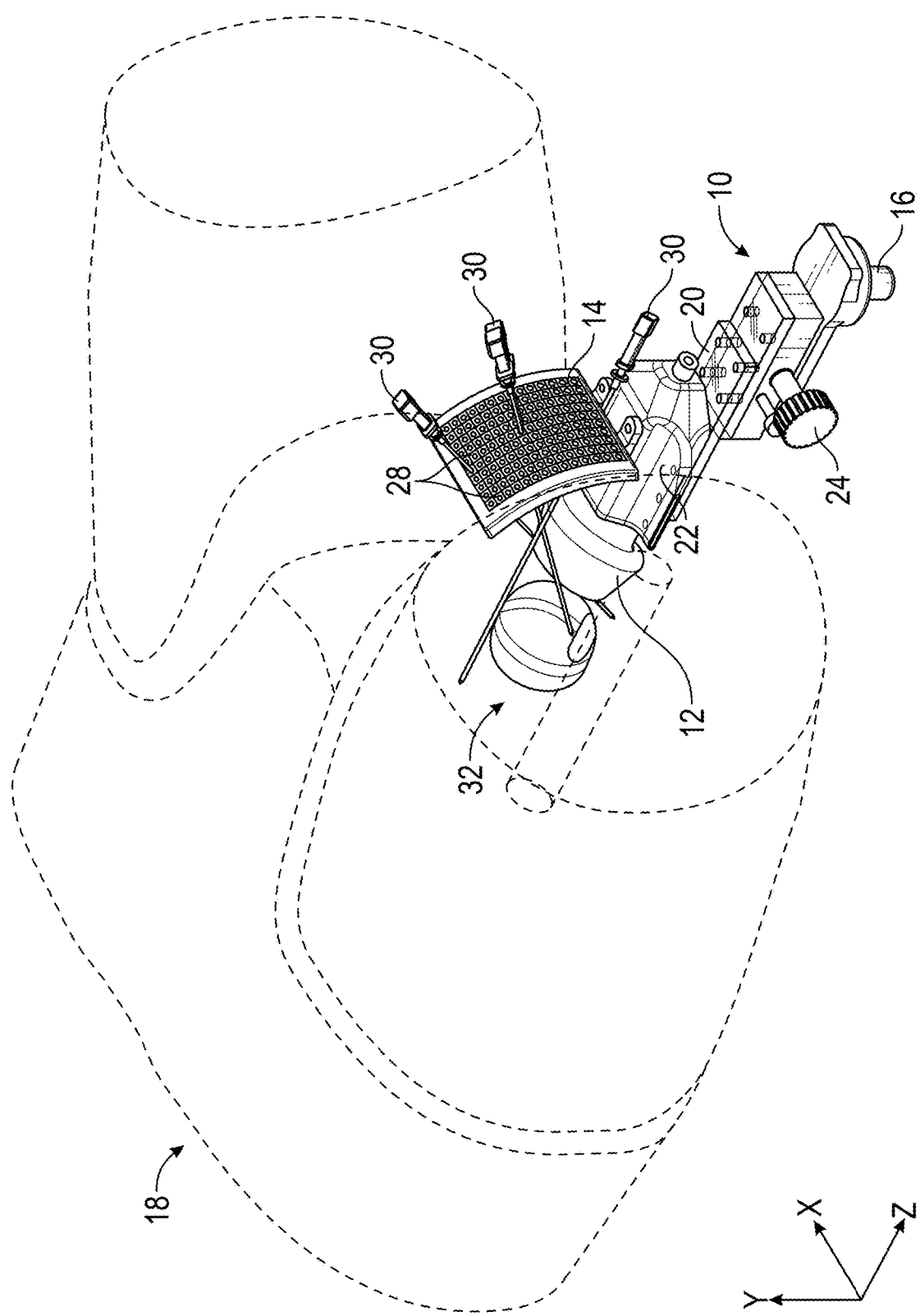
FIG. 2 illustrates an isometric view of the biopsy system shown in FIG. 1.

FIG. 2 illustrates an isometric view of the biopsy system shown in FIG. 1. As shown in FIG. 2, moveable stage 20 can be moveable in the directions indicated by arrow 26. Moveable stage 20 can support probe support 22 and grid 14 is a fixed manner. Grid 14 comprises a plurality of apertures 28 that can receive biopsy needles 30 and guide them towards a desired target, such as a portion of prostate 32.

Figure 3:
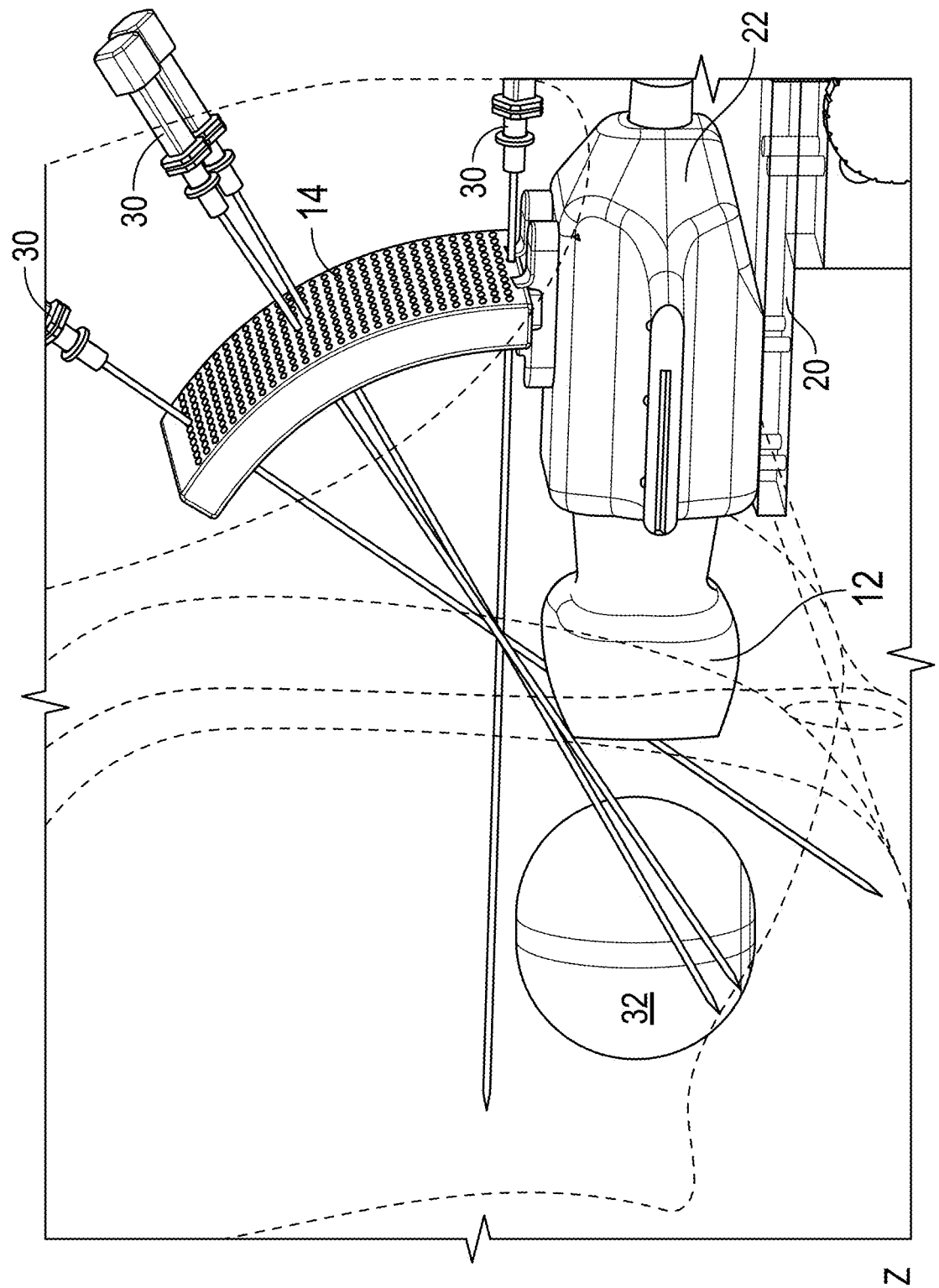
FIG. 3 illustrates an enlarged view of the biopsy system shown in FIGS. 1 and 2.
Figure 4:
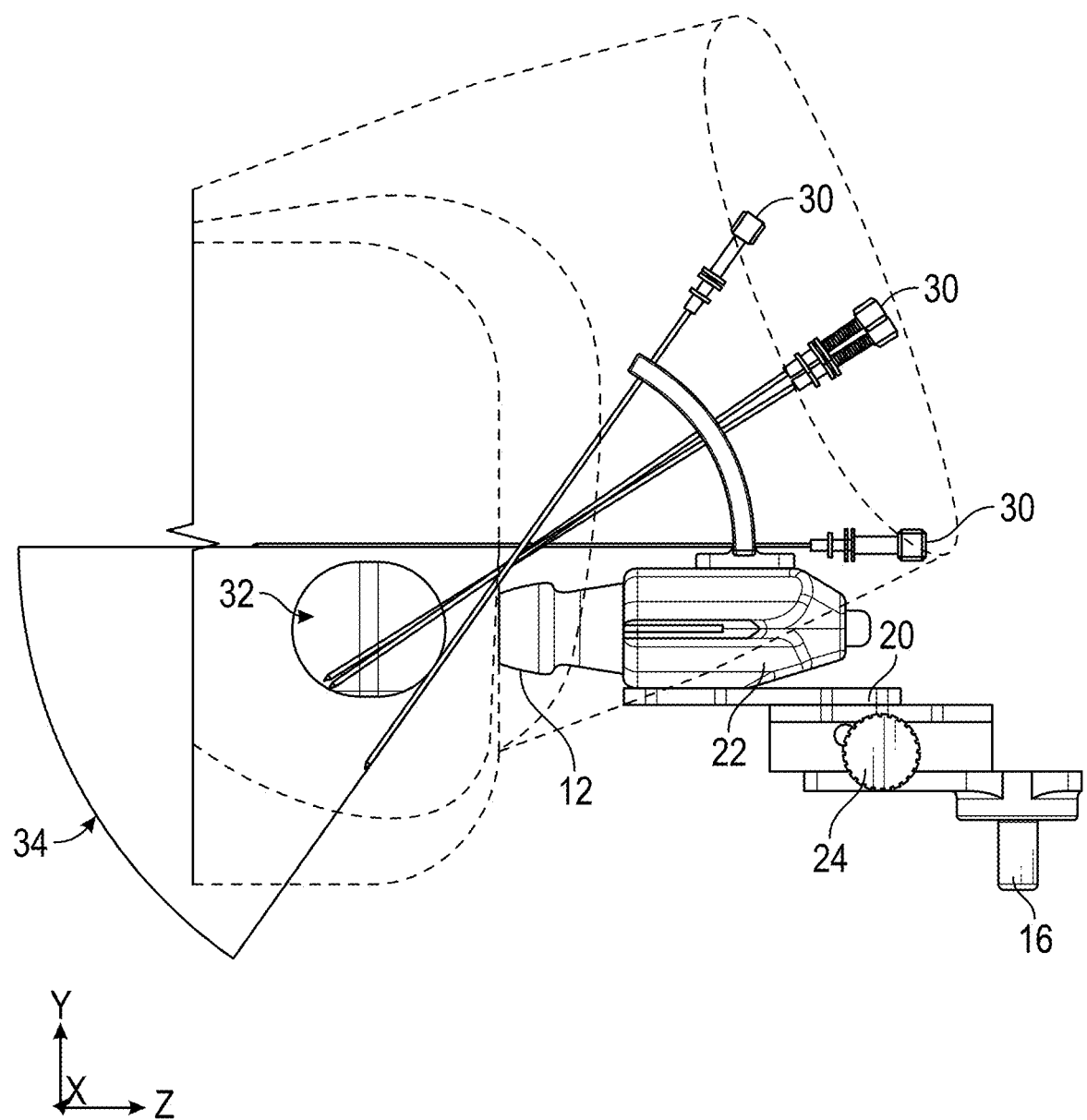
FIG. 4 illustrates another enlarged view of the biopsy system shown in FIGS. 1 and 2 showing the full coverage of the prostate with the proposed embodiment.

FIGS. 3 and 4 illustrate enlarged views of the biopsy system shown in FIGS. 1 and 2, further illustrating exemplary structural relationships between ultrasound probe 12, grid 14, probe support 22, and moveable stage 20. FIG. 4 also illustrates an effective area of prostate imaging coverage 34 achieved by ultrasound probe 12 when positioned transperineally.

Figure 5:
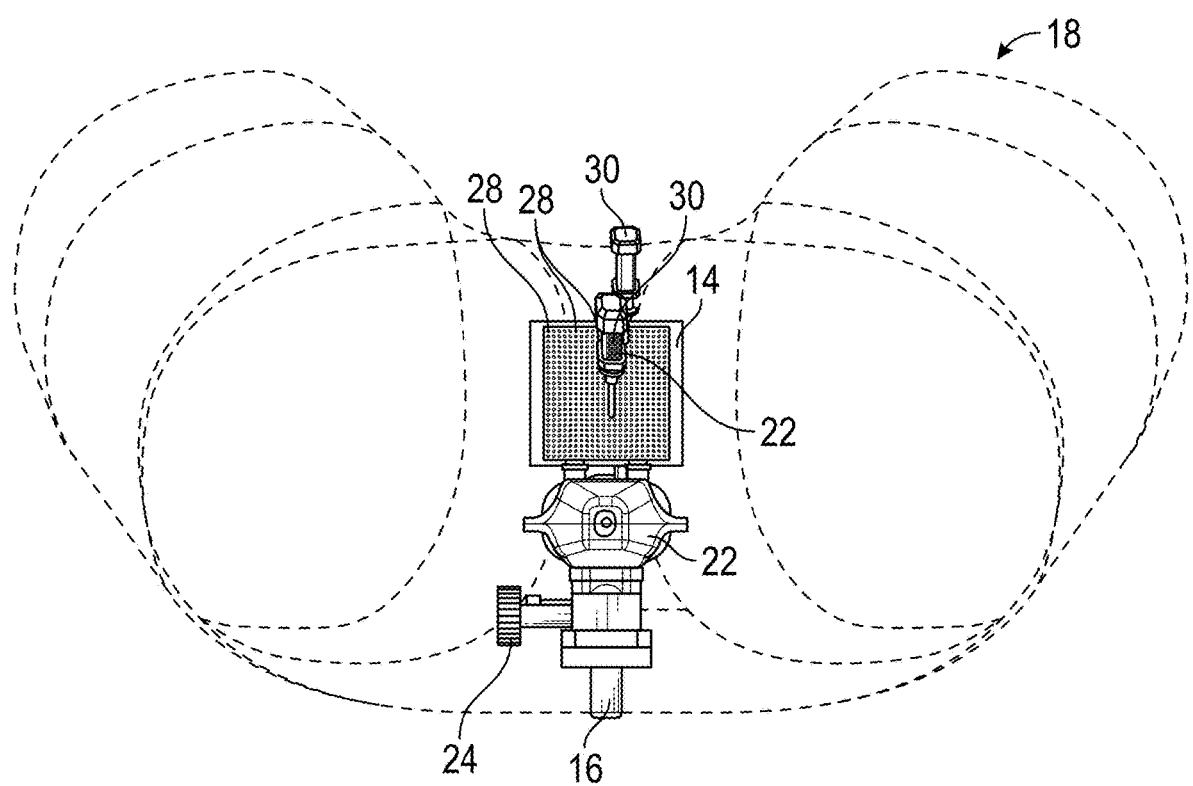
FIG. 5 illustrates a front view of the biopsy system shown in FIGS. 1 and 2.

FIG. 5 illustrates a front view of the biopsy system, showing additional features of the system, including an exemplary relative width of grid 14 to probe support 22. In this embodiment, grid 14 can be coupled to probe support 22 and have a ratio of grid 14 width to probe support 22 width of between 0.8:1 to 1.2:1, or between 0.9:1 and 1.1:1.

Grid 14 can be formed in various shapes, so long as the apertures are configured to guide needles to the location of the prostate. As shown in FIGS. 1-4, in some embodiments, grid 14 can be curved for guiding insertion of a plurality of biopsy needles into a patient's body. The curved grid can have a concave surface (curving inward) facing the patient, and a convex surface (curving outward) facing away from the patient. The radius of curvature (R) can vary depending on the desired application and the mounting arrangement of the grid.

The number and arrangement of apertures 28 can vary. In some embodiments, the distance between adjacent apertures is uniform in both the length and width directions. In other embodiments, the spacing and arrangement of apertures varies and/or is non-uniform. In some embodiments, the distance between adjacent apertures is within 2-6 millimeters. Apertures 28 can be marked with indicia to aid the surgeon in identifying a desired aperture, which in turn defines a needle trajectory or path that is defined by that aperture.

Figure 6:
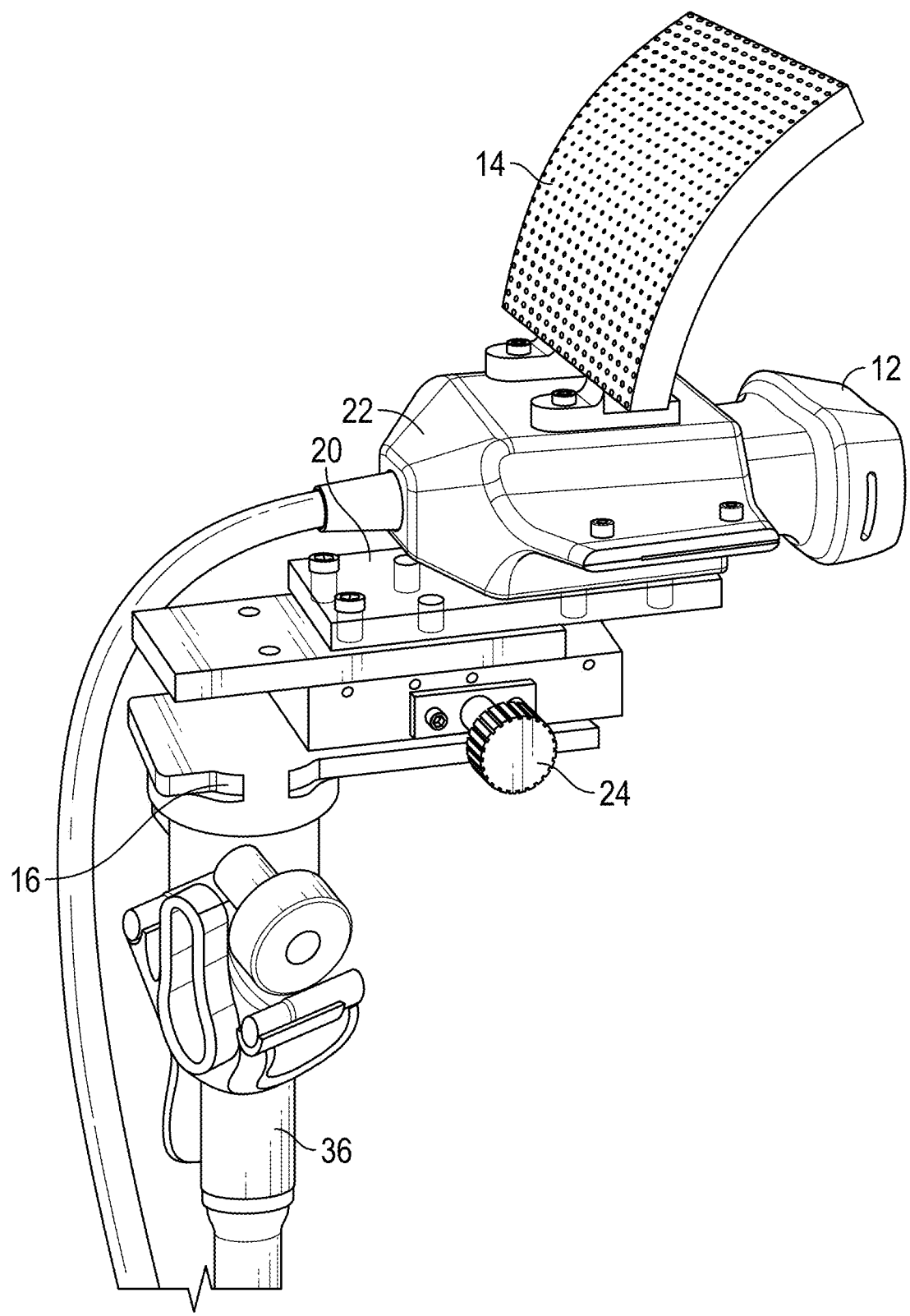
FIG. 6 illustrates an exemplary embodiment of the biopsy systems shown in FIGS. 1-5.

FIG. 6 illustrates an embodiment of the biopsy systems shown in FIGS. 1-5. As shown in FIG. 6, coupling member 16 is coupled to a passive positioning arm 36 to mount the biopsy system 10 in a desired location adjacent to a location (e.g., a hospital bed) where a patient can be supported during a biopsy procedure.

As discussed above, grid 14 can be pre-registered to the ultrasound probe so that its location and structure (including orientation of apertures), relative to ultrasound probe 12 and the images generated thereby, are known by the system. As discussed above, a passive or motorized arm or actuator can be used to position and secure the ultrasound probe 12 (and grid 14) in a desired position relative to the patient's perineum. Since prostate cancer lesions are invisible in ultrasound, the ultrasound images can be fused with preoperative images of higher resolution, such as images from a preoperative MRI. To achieve image fusion, images from ultrasound probe 12 can be obtained transperineally, with the patient in a supine position, and those images can be manually or automatically segmented to register them with the higher resolution preoperative images.

Fusion of the images can be achieved by retrieving one or more 3D image volumes (e.g., an MRI or CAT scan) acquired preoperatively from a data storage location and obtaining a first shape or surface model from that image, either manually or automatically. Ultrasound probe 12 can then be positioned transperineally and the patient's prostate can be imaged. In one embodiment, registration with the preoperative images can be achieved by segmenting the gland boundary in the ultrasound image and manually or automatically registering it to the preoperative scan image volume. Alternatively, other known techniques for registering ultrasound images and images from other modalities can be performed.

In addition, the registration and needle placement techniques described herein can be achieved without the use of any position tracking sensors (e.g., electromagnetic tracking systems) which is one of the main contributions of this technology. In particular, the 3D image provided by a 3D ultrasound transducer eliminates the need for position tracking which is conventionally used to combine 2D ultrasound images into a 3D volume (which is then registered to 3D MRI volume). Also, the position of the template grid mounted to the US probe is fixed relative to the 3D ultrasound volume provided by the 3D probe, which eliminates the need for sensors that track the location of the needle. The 3D volume provided by the 3D probe is superior to a 3D volume made by stitching 2D images with the help of a tracking device since it is acquired in nearly real-time whereas the latter is done manually and the quality of the reconstructed volume is user-dependent. Thus, the sensorless MR-US fusion systems described herein provides highly accurate imaging for improved needle guidance, while at the same time reducing costs and image fusion complications relative to conventional image fusion systems that are based on TRUS imaging.

Once the preoperative scan volume is registered to ultrasound probe 12, the ultrasound images can be generated in the same frame of reference as the preoperative scan images (either separately or in an overlapping manner). Because grid 14 has already been registered with ultrasound probe 12, the location of grid 14 and the respective needle trajectories of grid 14 are also known and can be displayed relative to the fused images.

The fused images of ultrasound probe 12 and the preoperative scan (e.g., MRI or CAT scan) provide improved guidance of the biopsy needs toward the suspect pathological tissue. In some embodiments, the trajectories associated with one or more apertures 28 are indicated on a display screen, along with one or more of the fused images, to guide the surgeon. The selection of one or more trajectories to the area of interest also necessarily takes into consideration the pubic arch and other internal structures of the particular patient so that contact with those structures can be avoided during the delivery of the biopsy needles into the patient.

FIGS. 7-11 illustrate another embodiment of a biopsy system including a frame that supports an ultrasound probe for transperineal positioning and a template grid for needle guidance. The embodiment shown in FIGS. 7-11 differs from the previous embodiment by disclosing a different type of grid 114.

As shown in FIGS. 7-11, grid 114 comprises two portions 114A and 114B which extend laterally in different directions from the location of the ultrasound probe. Grid portion 114A extends in a first lateral direction from probe support 122 and grid portion 114B extends in a second, opposite lateral direction from probe support 122. In this manner, apertures 128 provide different approach paths to prostate 132 than those of the previous embodiment (in which grid 14 and its associated apertures 28 extended above ultrasound probe 12 rather than laterally to the side of ultrasound probe 12).

Figure 7:
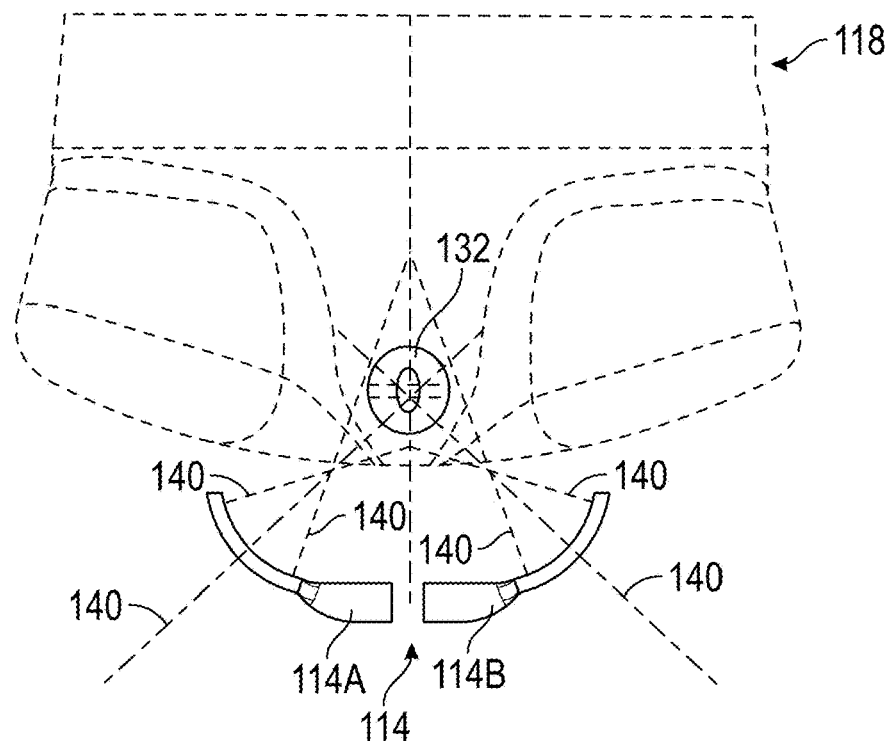
FIG. 7 illustrates another embodiment of a biopsy system that has a laterally-extending template grid.
Figure 8:
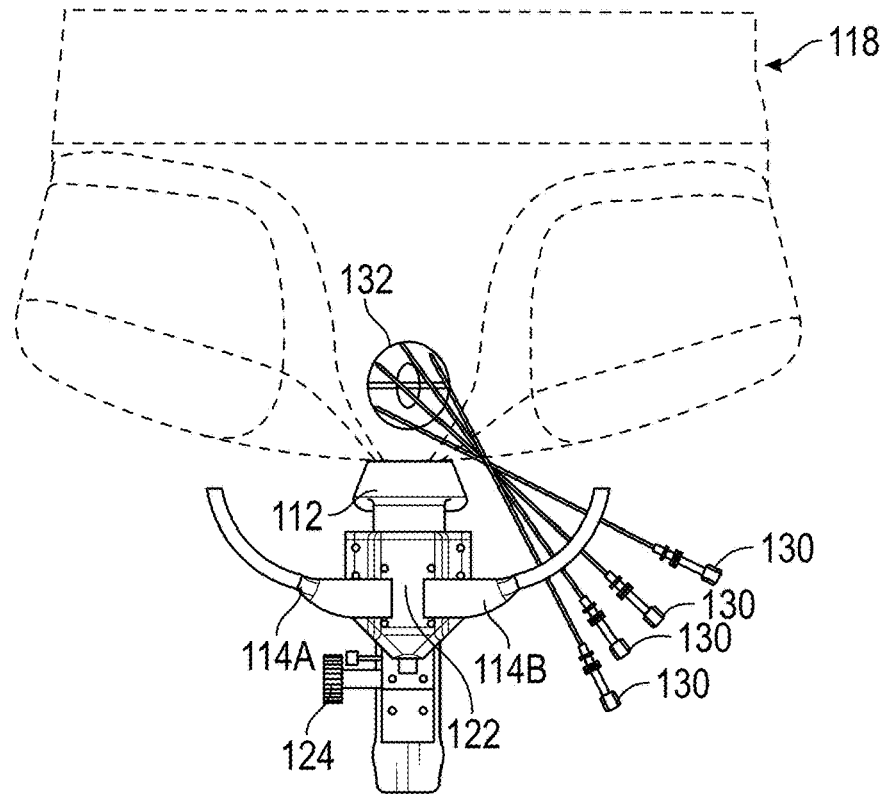
FIG. 8 illustrates another view of the embodiment of FIG. 7, showing the template grid of FIG. 7 coupled to a frame and the workspace it covers.
Figure 9:
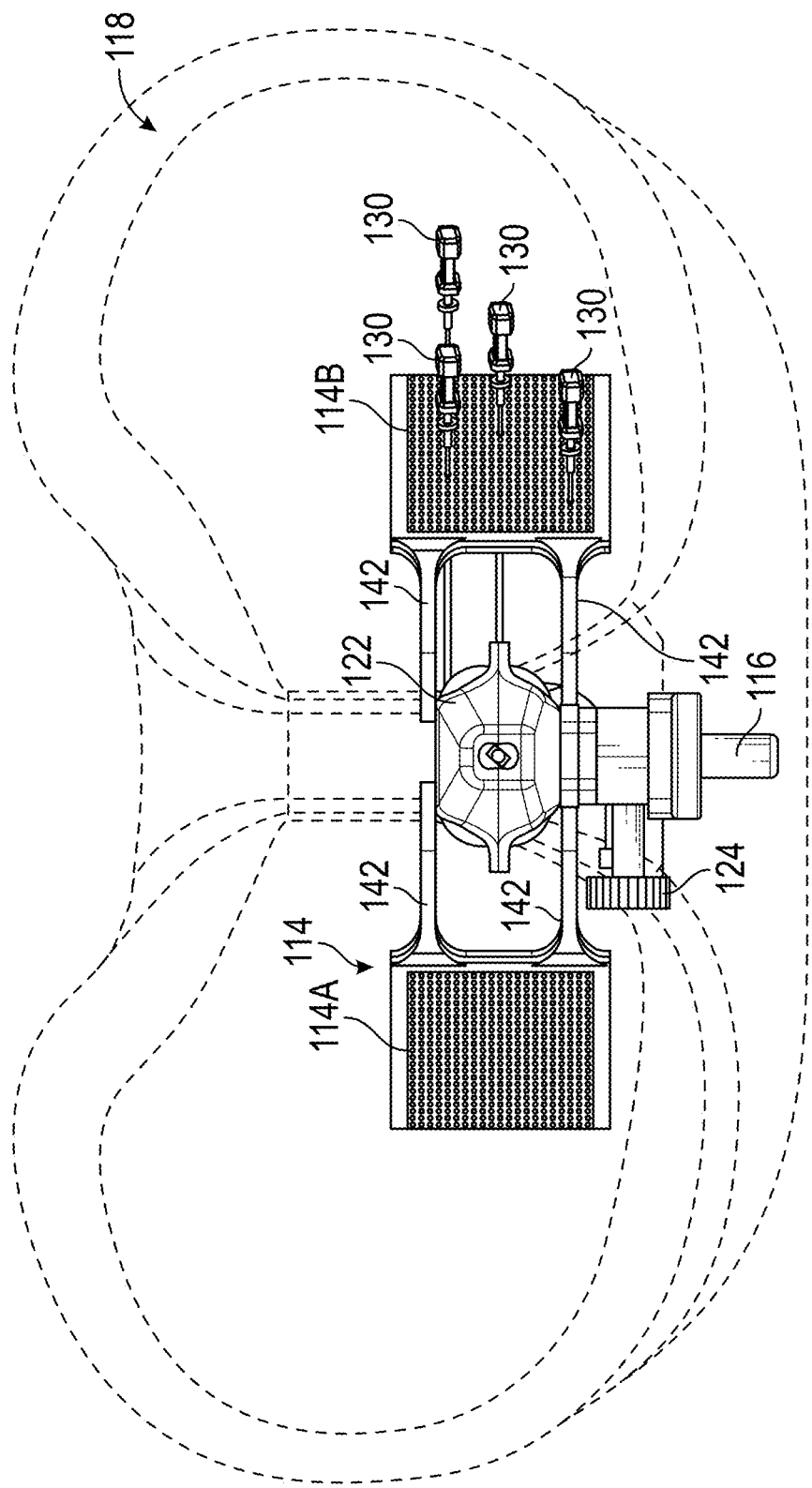
FIG. 9 illustrates a front view of the biopsy system shown in FIG. 8.
Figure 10:
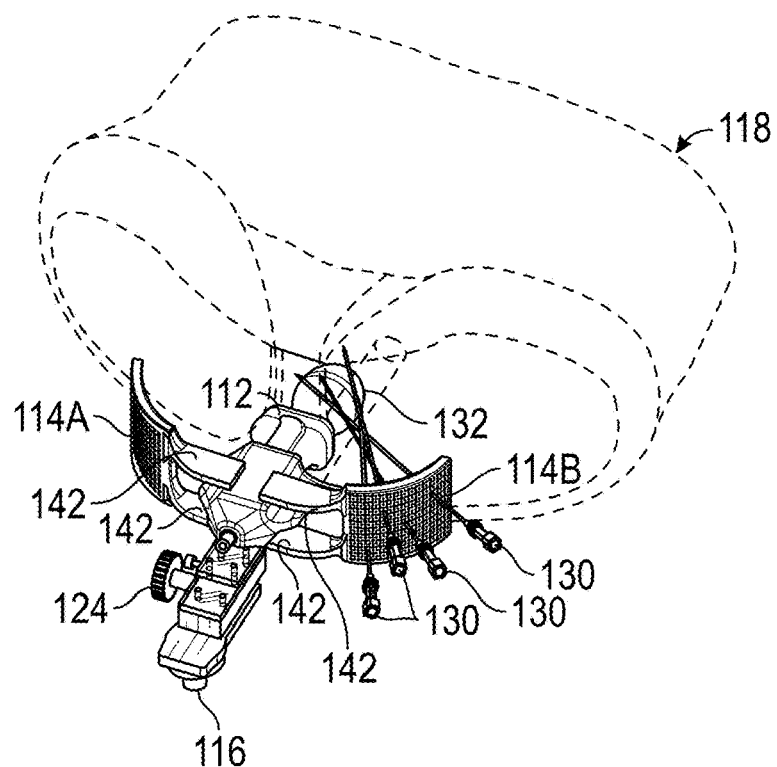
FIG. 10 illustrates an isometric view of the biopsy system shown in FIG. 8.
Figure 11:
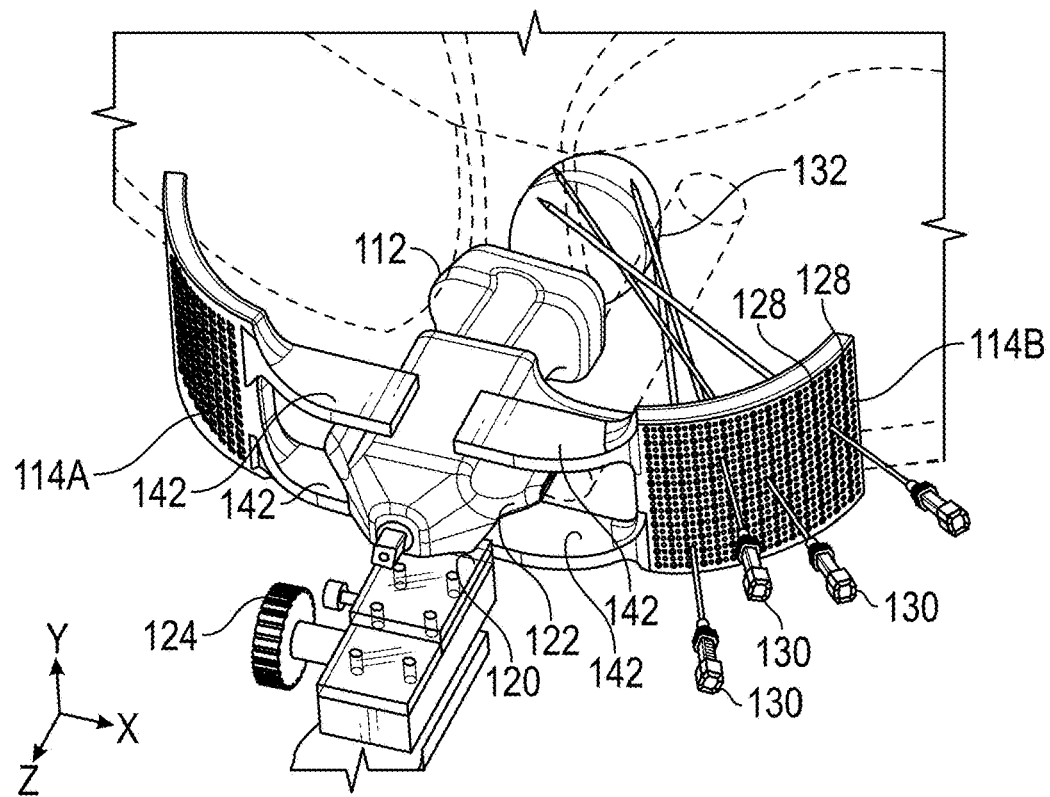
FIG. 11 illustrates an enlarged view of the biopsy system shown in FIG. 10.

As shown in FIG. 7, each aperture 128 defines a trajectory 140 based on its location and orientation on grid portions 114A, 114B. Using the image fusion and display methods discussed herein, one or more available trajectories 140 can be displayed during the procedure to allow for the selection of the best path to the tissue area of interest of the prostate. Grid portions 114A, 114B can be generally flat or they can be curved as shown in FIGS. 7 and 8. Referring to FIG. 9, each grid portion 114A, 114B can be coupled to the probe support 122 by one or more arm members 142. Grid portions 114A, 114B can be coupled to one another or they can be independently coupled and moveable relative to probe support 122.

During the transperineal prostate biopsy, the patient is generally positioned supine on his back with legs bent and/or elevated. Elevating the legs can improve access to the perineal area during the procedure.

Figure 12:
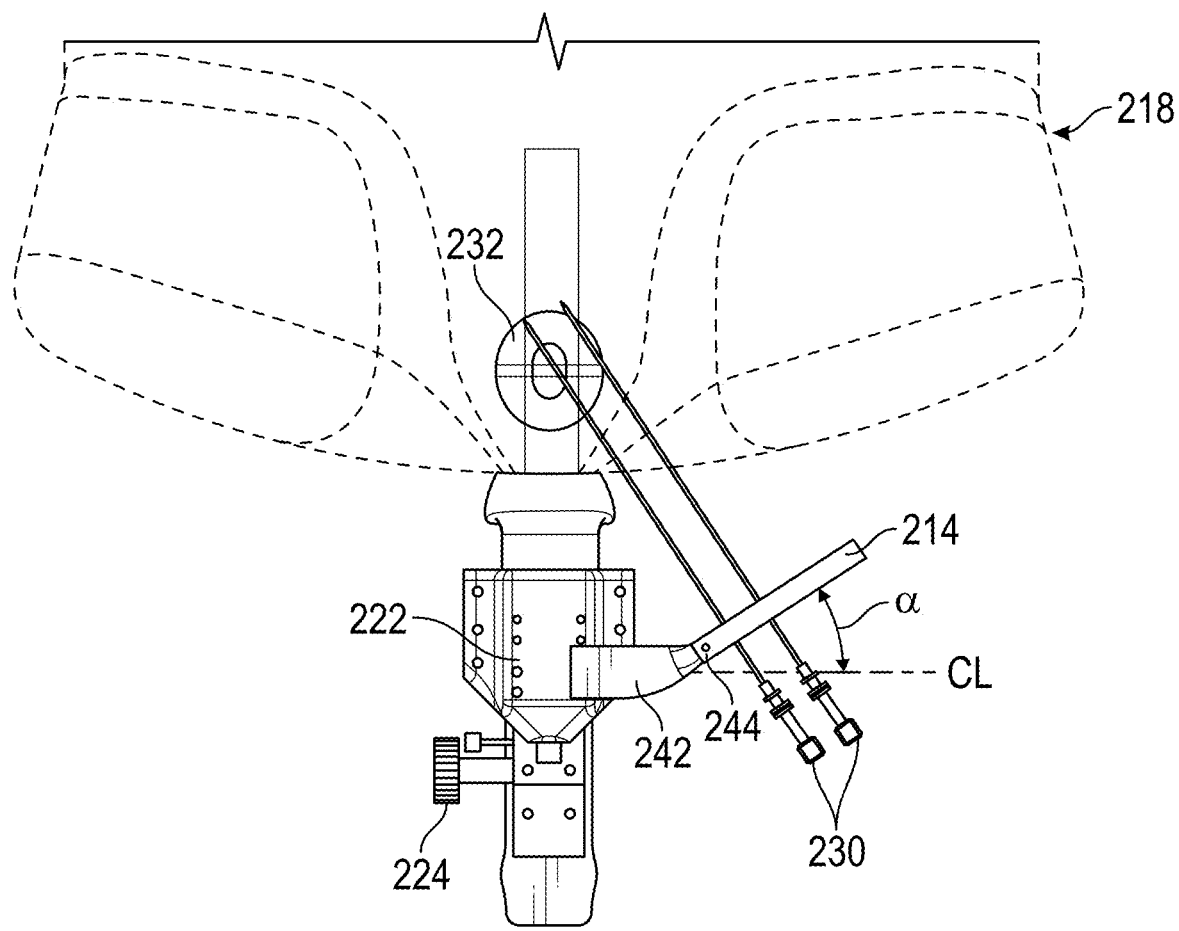
FIG. 12 illustrates the biopsy system shown in FIG. 8, showing the hinged template grid in a first known position, forming a first angle relative to a centerline of an arm member.
Figure 13:
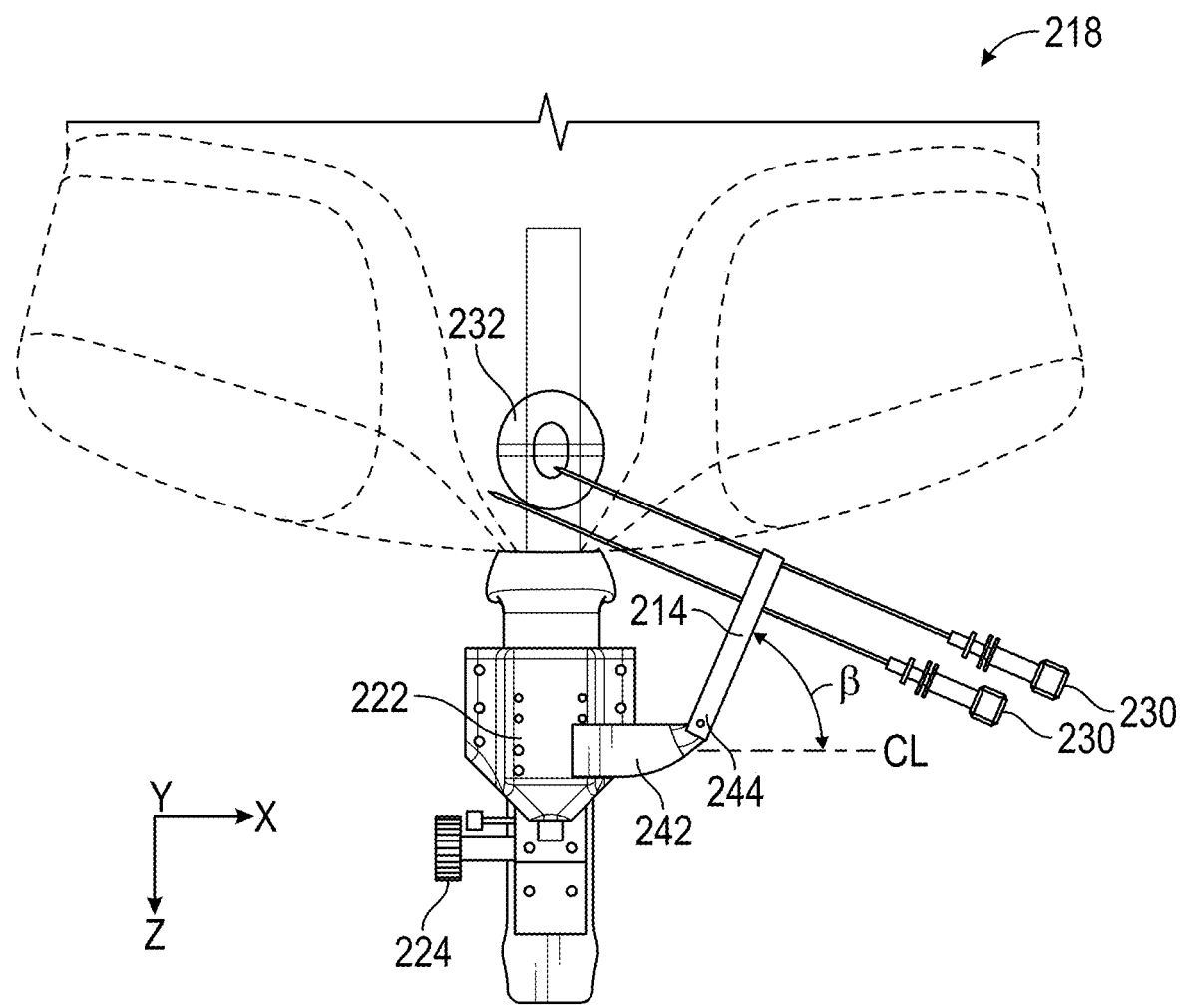
FIG. 13 illustrates the biopsy system shown in FIG. 8, showing the hinged template grid in a second position forming a second known angle relative to a centerline of an arm member.
Figure 14:
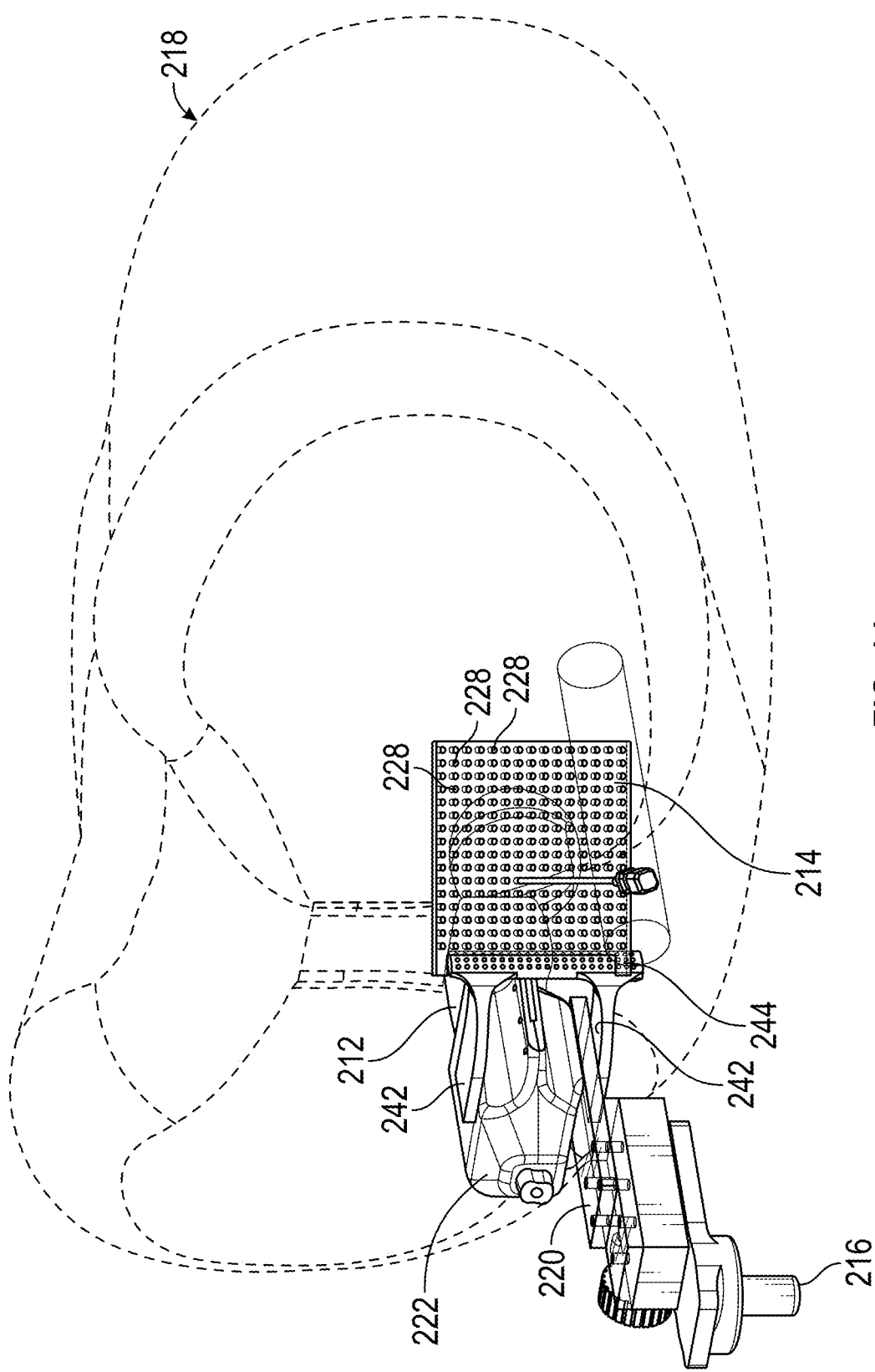
FIG. 14 illustrates a perspective view of the hinged template grid shown in FIG. 12.

FIGS. 12-14 illustrate another embodiment in which one or more grid members 214 extend laterally from at least one side of probe support 222. Grid member(s) 214 can be moveably coupled to probe support 222. For example, as shown in FIGS. 12-14, grid member 214 is pivotably coupled to one or more arm members 242, which are in turn coupled to probe support 222. In this manner, grid member 214 can pivot about hinged portion 244 and provide different trajectories through apertures 228 depending on the orientation of (i.e., angle of) grid member relative to arm members 242. FIG. 12 illustrates grid member 214 in a first position (forming a first angle α relative to a centerline of arm member 242) and FIG. 13 illustrates grid member 214 in a second position (forming a second angle β relative to a centerline of arm member 242). As shown in FIGS. 12 and 13, the different angle provide different alignments of apertures 228 with trajectories that intersect with prostate 232.

Although grid 214 is illustrated as being generally flat in FIGS. 12 and 13, it should be understood that other shapes are possible, including for example, a curved grid structure like that shown in other embodiments herein.

Figure 15:
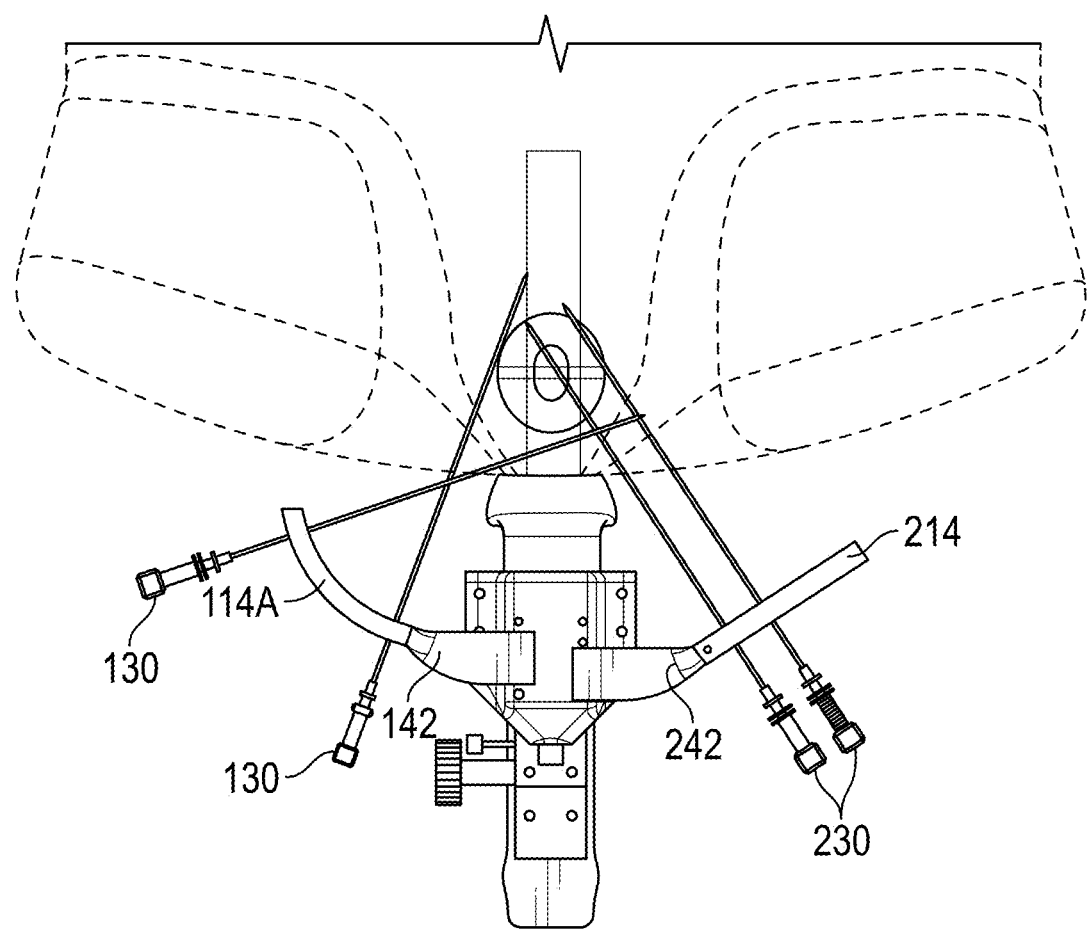
FIG. 15 shows a combination of different template grids that can be used in a biopsy system and the effect on trajectories associated with each.

FIG. 15 shows a comparison of different template grids and the effect on trajectories associated with each. As can be understood by viewing the different resulting trajectories indicated by the locations of biopsy needles 130, 230, the systems have different advantages and disadvantages. For example, relative to curved grid 114, hinged grid 214 can potentially be more intuitive to work with and provide greater uniform accuracy over the workspace. On the other hand, relative to curved grid 114, hinged grid 214 can be more prone to errors and pubic arch interference and, as a result of its ability to pivot about arm member 242, can be more complex to work with in some circumstances.

Figure 16:
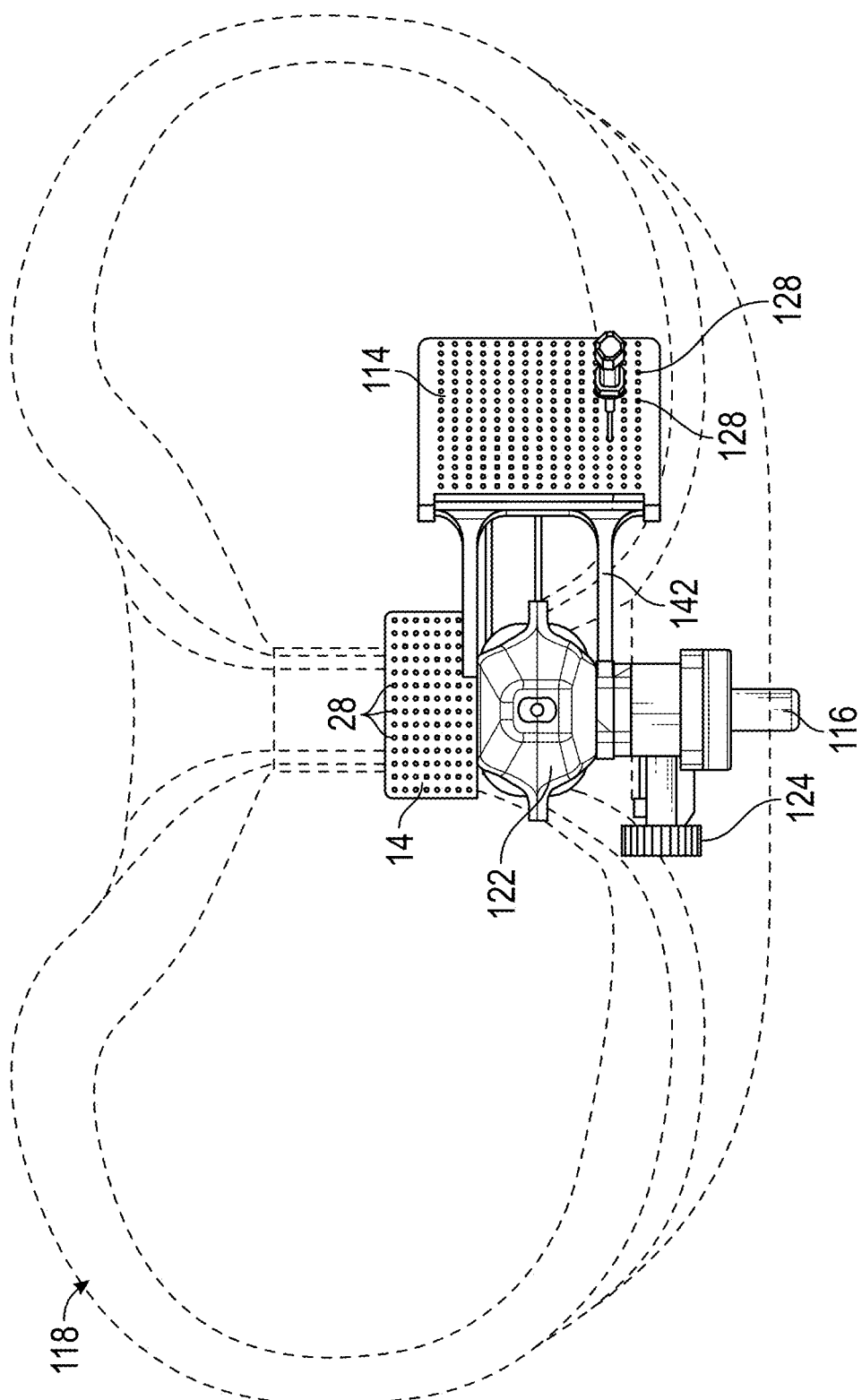
FIG. 16 illustrates another alternative of a biopsy system where a top grid is used in combination with a laterally-extending grid.
Figure 17:
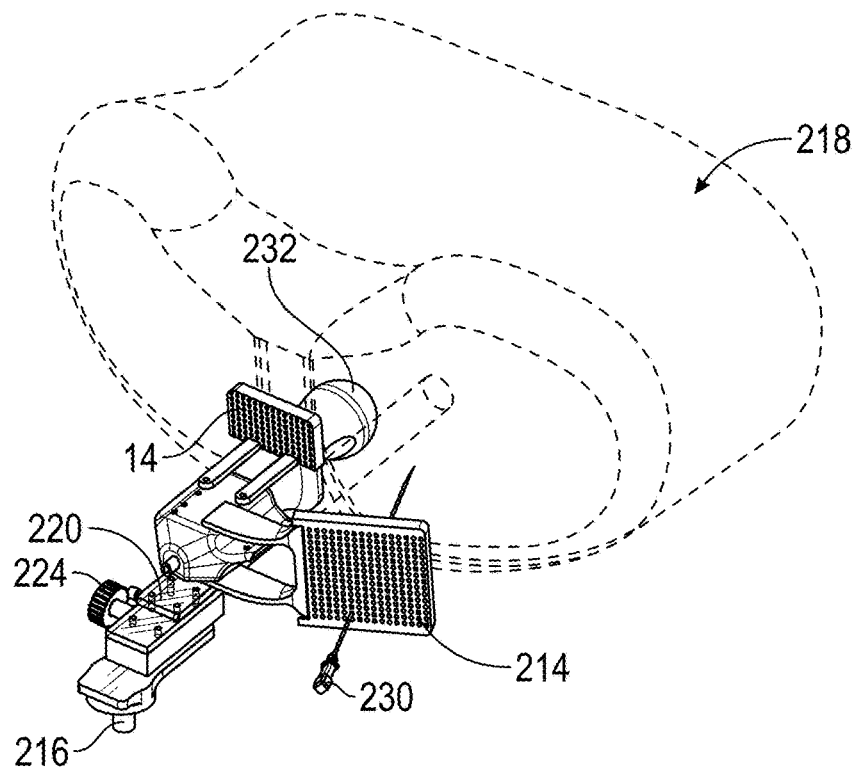
FIG. 17 illustrates a perspective view of the design embodiment showed in FIG. 16

If desired, any combination of two or more of the grids disclosed herein can be used. For example, FIG. 15 illustrates the potential use of two laterally-extending grids that are different from one another. FIG. 16 illustrates another alternative where a top grid 14 is used in combination with a laterally-extending grid 114. FIG. 17 illustrates another embodiment that combines a top grid 14 with a laterally-extending hinged grid 214. Top grid 14 can also be hinged if desired. Combining different grid options in this manner can allow for greater flexibility in selecting trajectories to the tissue area of interest, including a greater number of trajectory options that avoid pubic arch interference.

Figure 18:
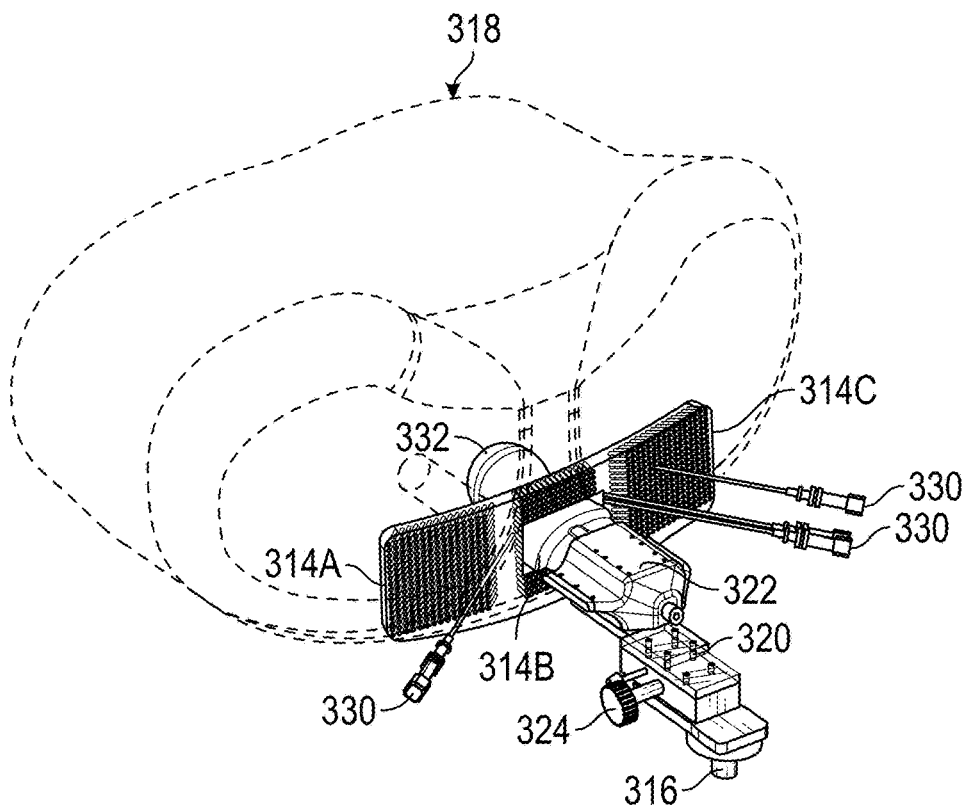
FIG. 18 illustrates another embodiment of a biopsy system with both a central and laterally-extending grid in a single-piece rigid template with angled needle guides.
Figure 19:
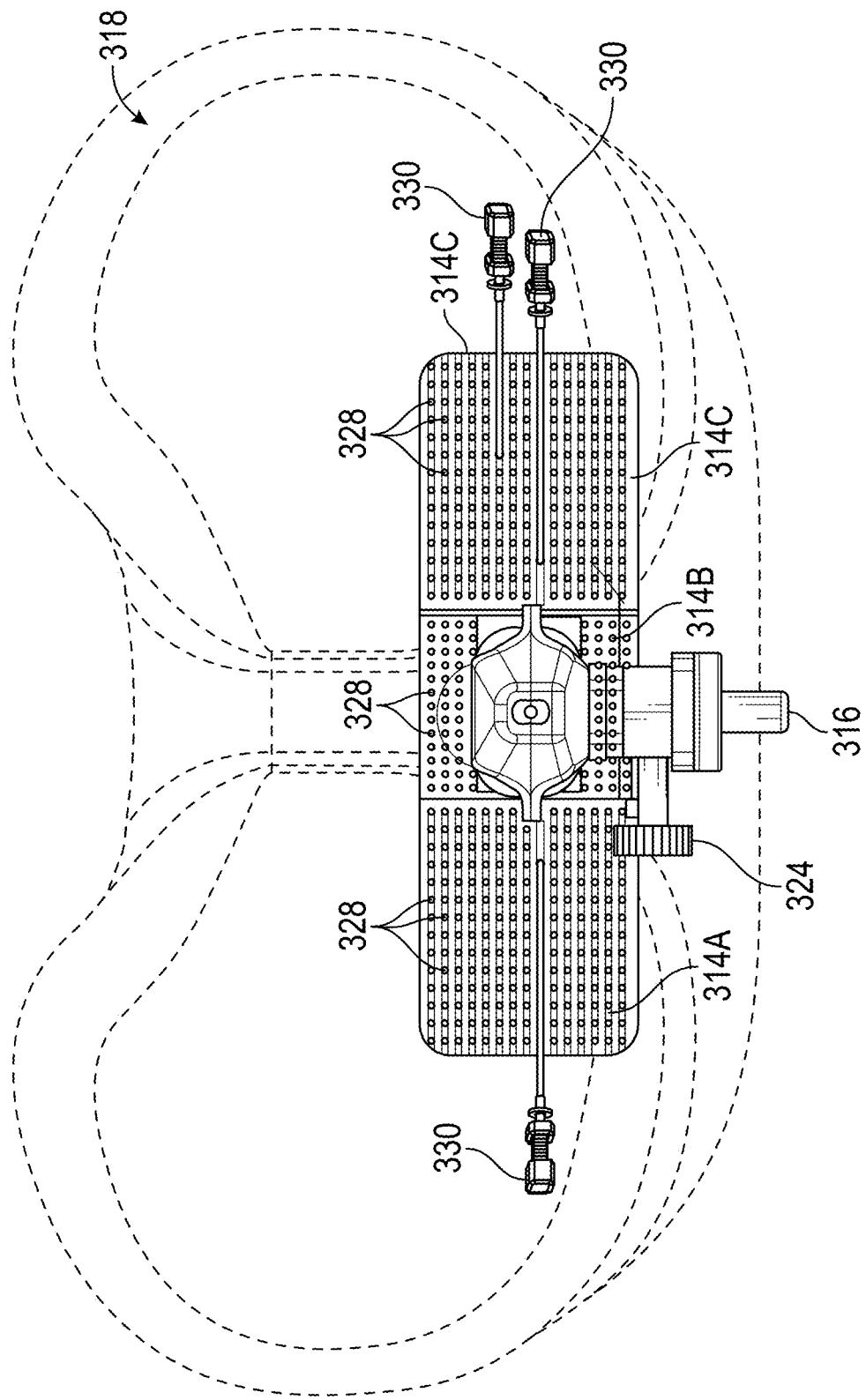
FIG. 19 shows a front view of the biopsy system of FIG. 18.
Figure 20:
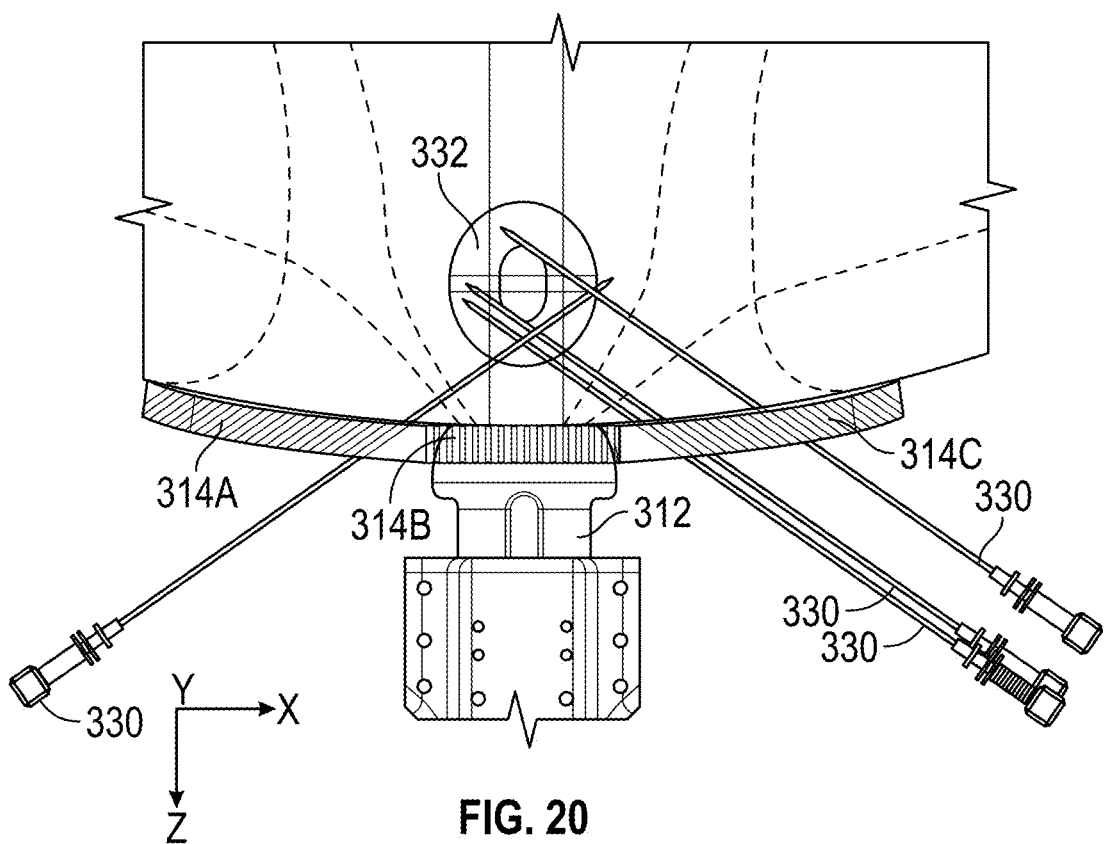
FIG. 20 shows a top view of the biopsy system of FIG. 18, with the template grid shown in cross section.

FIGS. 18-20 illustrate another embodiment in which a template grid with three portions 314A, 314B, and 314C is provided to establish a plurality of different possible trajectories for delivery of biopsy needs 330. FIG. 18 shows an isometric view of the biopsy system, FIG. 19 shows a front view, and FIG. 20 shows a top view with grid 314 shown in cross section.

As shown in FIGS. 18-20, two laterally-extending grid portions 314A, 314C are provided adjacent a central grid portion 314B. Central grid portion 314B provides additional approach paths (e.g., above and/or below ultrasound probe 312) to gain access to targeted tissue in the prostate. Laterally-extending grid portions 314A, 314C can be curved (e.g., contoured to match the natural curvature of a patient's body in the corresponding area) and central grid portion 314B can be generally flat as shown in FIG. 20, or it can have a slight curvature.

In some embodiments, as best shown in FIG. 20, a plurality of apertures 328 in the laterally-extending grid portions 314A, 314C can be configured to provide needle guidance along paths that are angled inward towards the prostate. In this manner, one or more apertures in grid portion 314A are angled in a first direction and one or more apertures in grid portion 314C are angled in a second direction that is different from the first direction. In some embodiments, one or more pathways defined by grid portion 314A are generally perpendicular to one or more pathways defined by grid portion 314C (i.e., forming an angle of overlap as seen from above in FIG. 20, of between about 75 and 105 degrees). As shown in FIG. 20, a plurality of apertures 328 in central grid portion 314B can be configured to provide needle guidance along paths that are generally parallel to one another.

Figure 21:
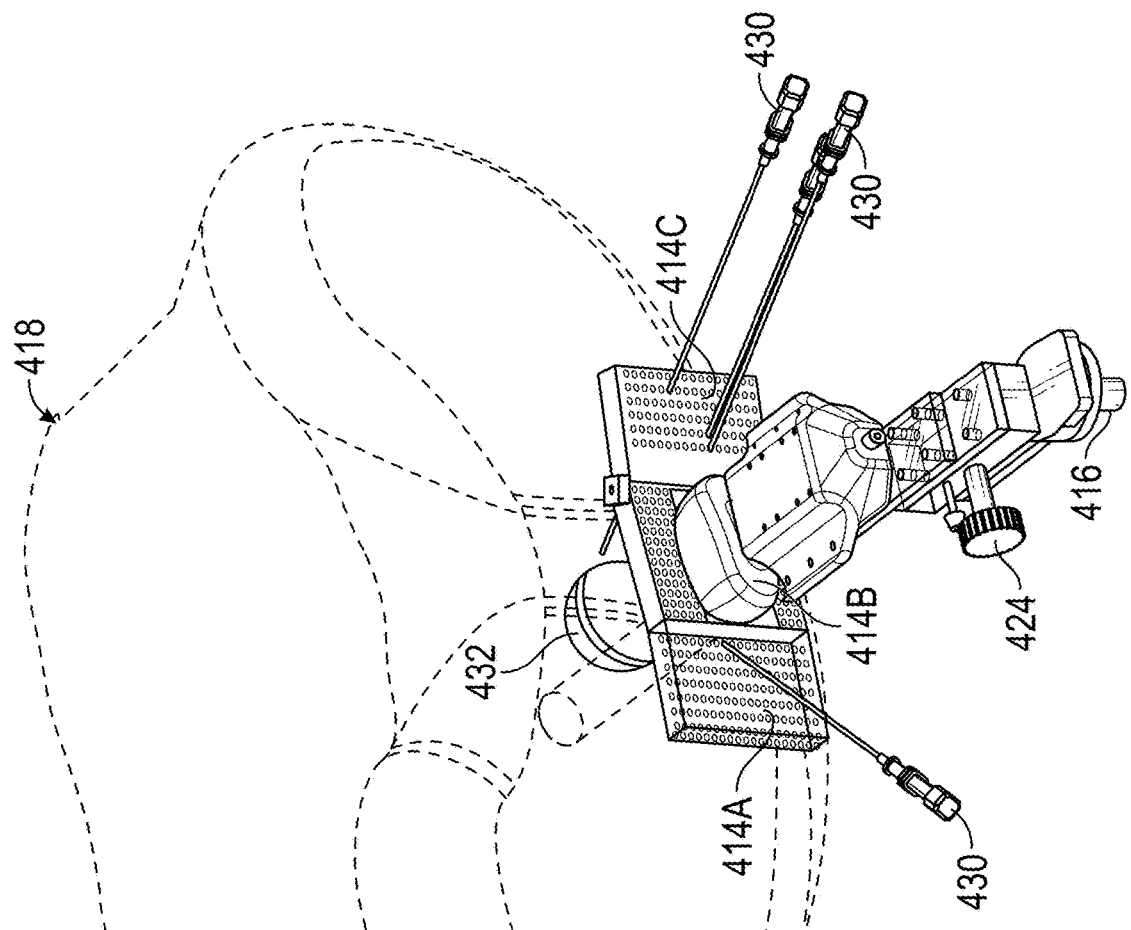
FIG. 21 illustrates another embodiment of a biopsy system that comprises a template grid with two laterally-extending grid portions adjacent a central grid portion.
Figure 22:
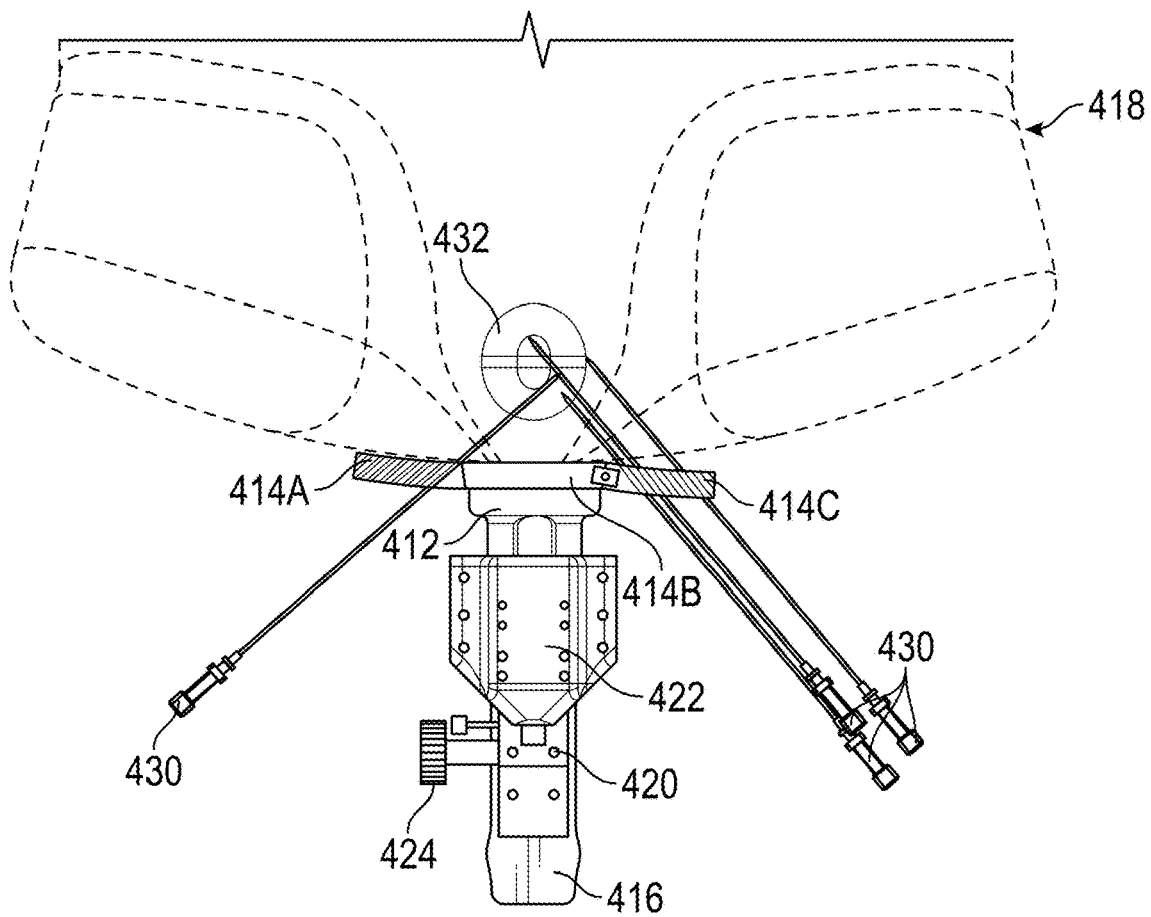
FIG. 22 shows a top view of the biopsy system shown in FIG. 21, illustrating a hinged laterally-extending grid portion.

FIGS. 21 and 22 show another embodiment of a biopsy system that comprises a template grid with two laterally-extending grid portions 414A, 414C provided adjacent a central grid portion 414B. As shown in FIG. 22, central grid portion 414B can be configured to provide additional approach paths (e.g., above and/or below ultrasound probe 412) to gain access to targeted tissue in the prostate. Like the embodiments shown in FIGS. 18-20, laterally-extending grid portions 414A, 414C can be curved and central grid portion 414B can be generally flat or it can have a slight curvature.

In this embodiment, one or both of laterally-extending grid portions 414A, 414C can be moveably coupled to central grid portion 414B (either directly or indirectly through a connecting member or arm). As shown in FIG. 21, for example, a pivot member can be provided to couple laterally-extending grid portion 414C to central grid portion 414B, which increases the number of possible trajectories available. By making slight adjustments to the position of laterally-extending grid portion 414C, such as pivoting it outward from the patient from a first position (e.g., shown in FIG. 20) to a second position (e.g., shown in FIG. 21), additional trajectories can be achieved.

As discussed above, registration of the template grid with the transperineal ultrasound images and subsequent fusion of the ultrasound images with higher resolution, preoperative images (e.g., MRI or CAT scans) can result in accurate and non-invasive imaging of the prostate. In another embodiment, template grids that are patient specific can be designed and constructed. Patient-specific grids can further improve needle guidance by increasing the accuracy of trajectories that target a desired tissue area of interest while at the same time avoiding pubic arch anatomy specific to the patient.

Figure 23A:
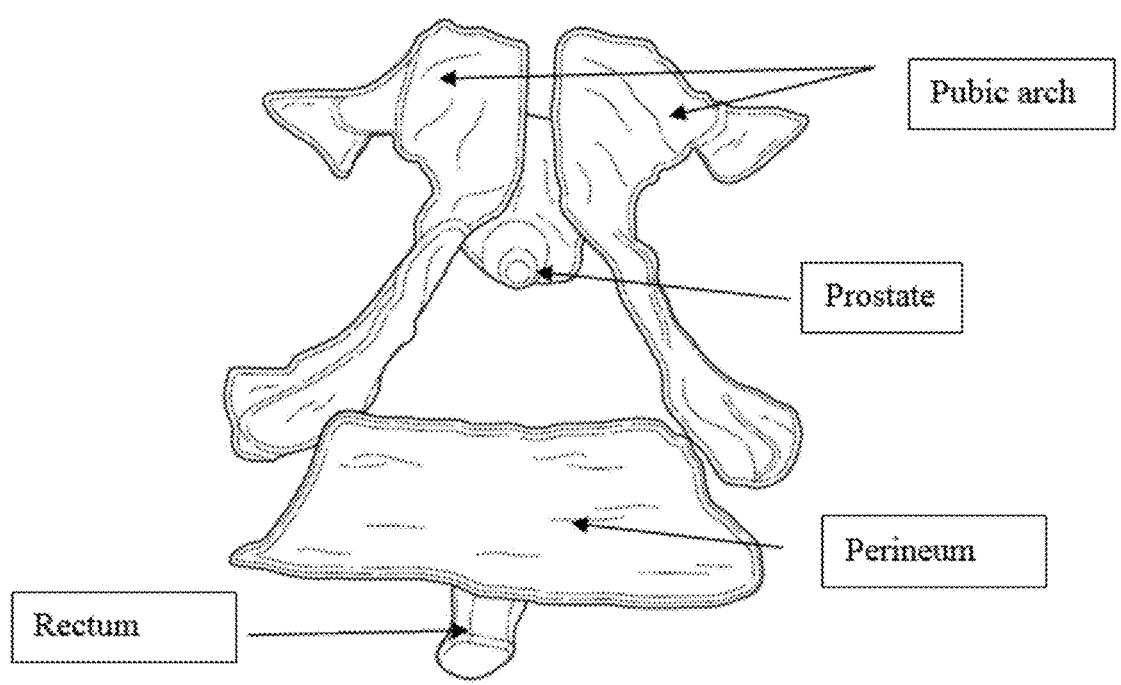
FIG. 23A illustrates an exemplary segmented 3D model of a prostate, pubic arch, and perineum.
Figure 23B:
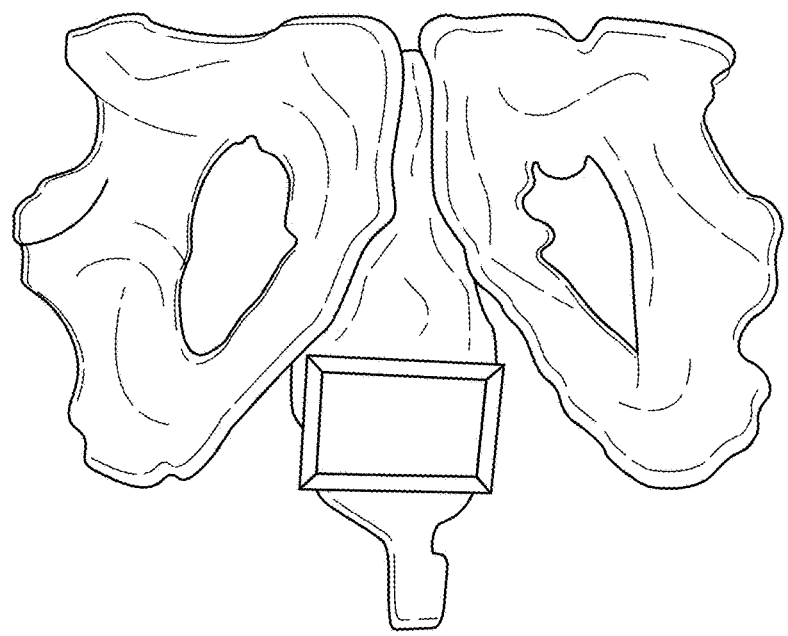
FIG. 23B illustrates a solid model created using segmented 3D models obtained from the segmented 3D model shown in FIG. 23A.
Figure 23C:
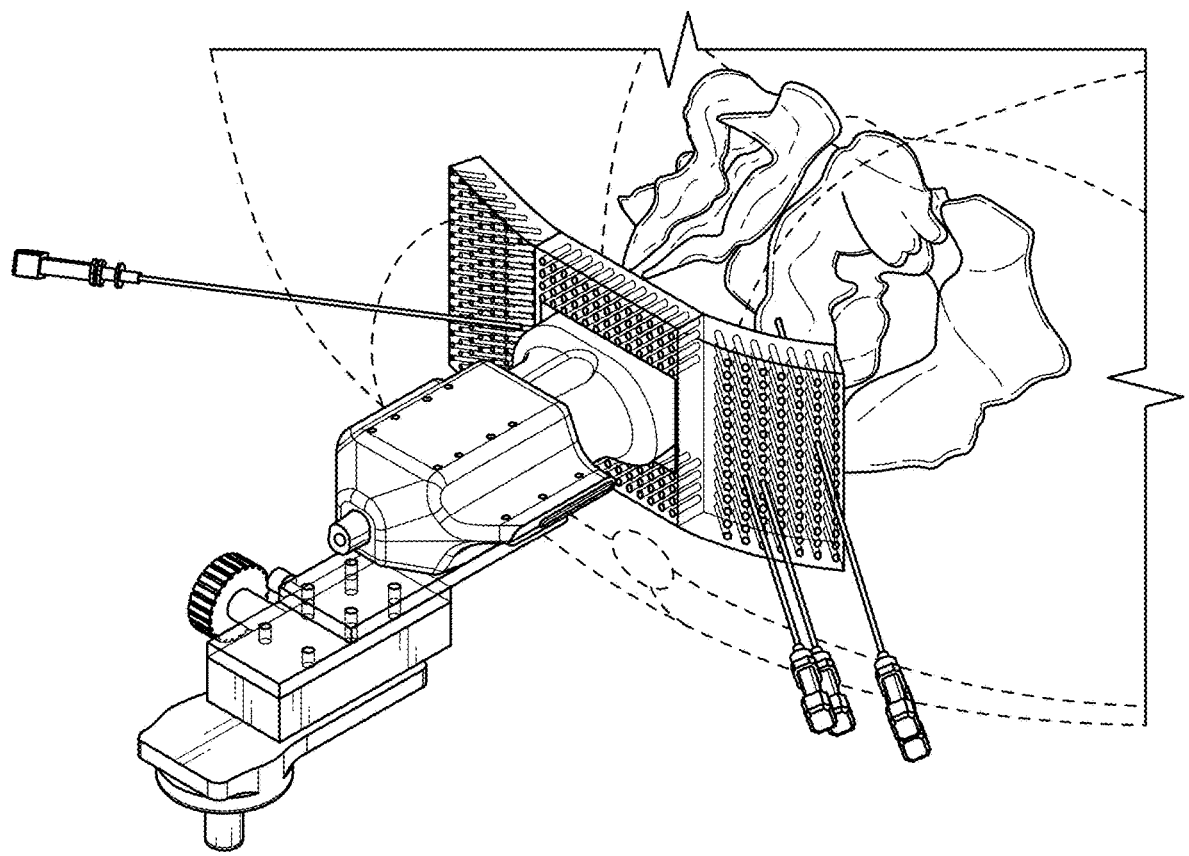
FIG. 23C illustrates the use of solid modeling to identify desired trajectories that avoid pubic area interference and can be used to develop and design specific template grids that will provide the desired trajectories.

FIGS. 23A-23C illustrate a method for creating a patient-specific template grid. Initially, a patient's pelvic region can be imaged by a high-resolution imaging modality (e.g., MRI or CAT scans). Those images can be used to obtain segmented 3D models of the patient's prostate and adjacent areas (e.g., perineal space, pubic arch, prostate, and rectum). Segmented 3D models can be obtained using available medical imaging software, such as by using the open source software package 3D Slicer. FIG. 23A illustrates an exemplary segmented 3D model of a prostate, pubic arch, and perineum.

The 3D model can be used with other modeling programs to visualize real life patients systems and model the functions of possible template grids. For example, the segmented 3D model can be converted to a file that can be used with a solid modeling CAD program, such as a .stl file that can be used with SOLIDWORKS®, published by Dassault Systemes.

FIG. 23B illustrates a solid model created using segmented 3D models obtained from MRI scans. As shown in FIG. 23C, the solid model aids in the identification of appropriate biopsy trajectories that avoid pubic arch interference. The identification of such trajectories is used to then develop specific template grids that can achieve those desired trajectories.

Figure 24:
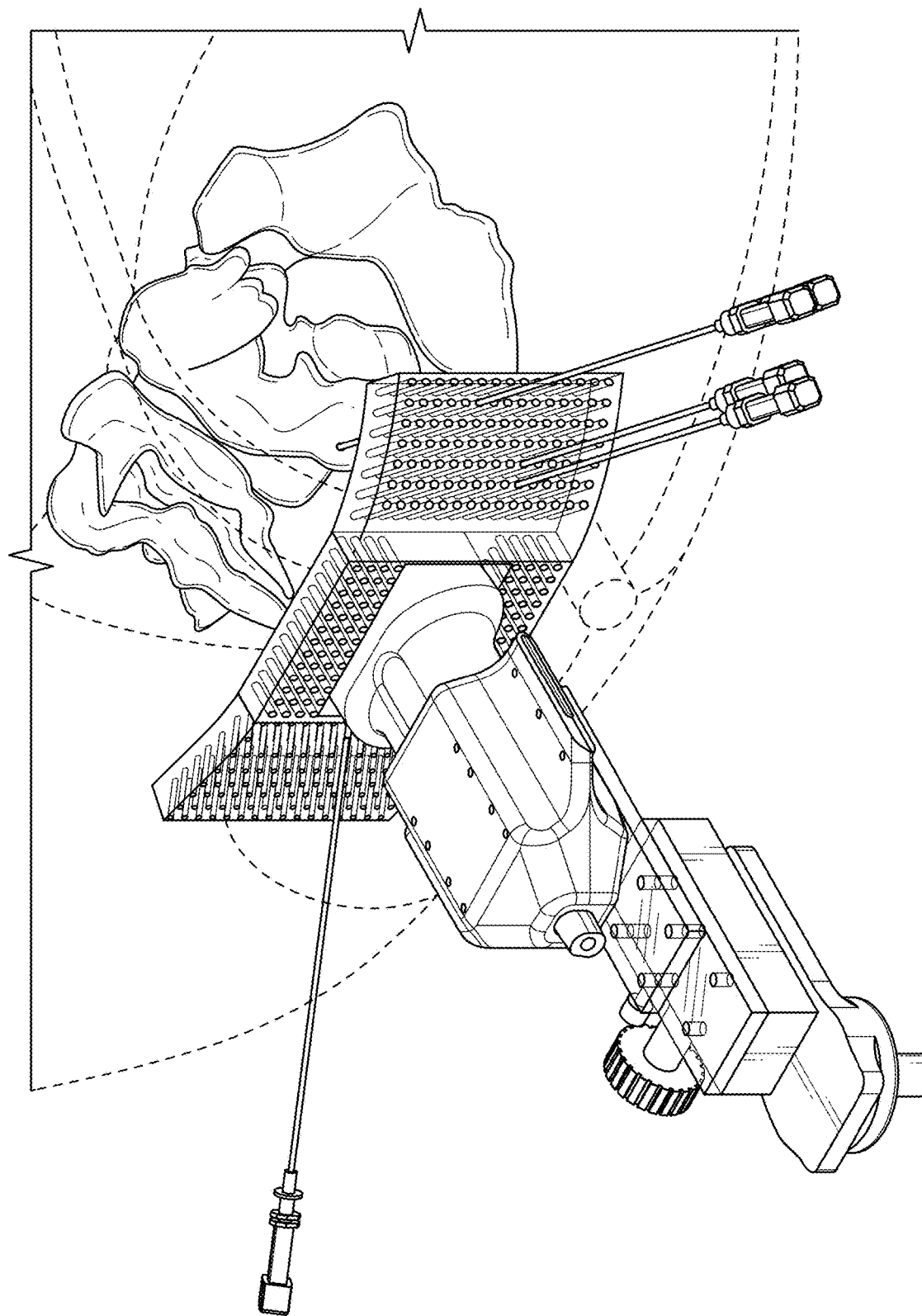
FIG. 24 shows an enlarged view of the biopsy system shown in FIG. 23A.
Figure 25:
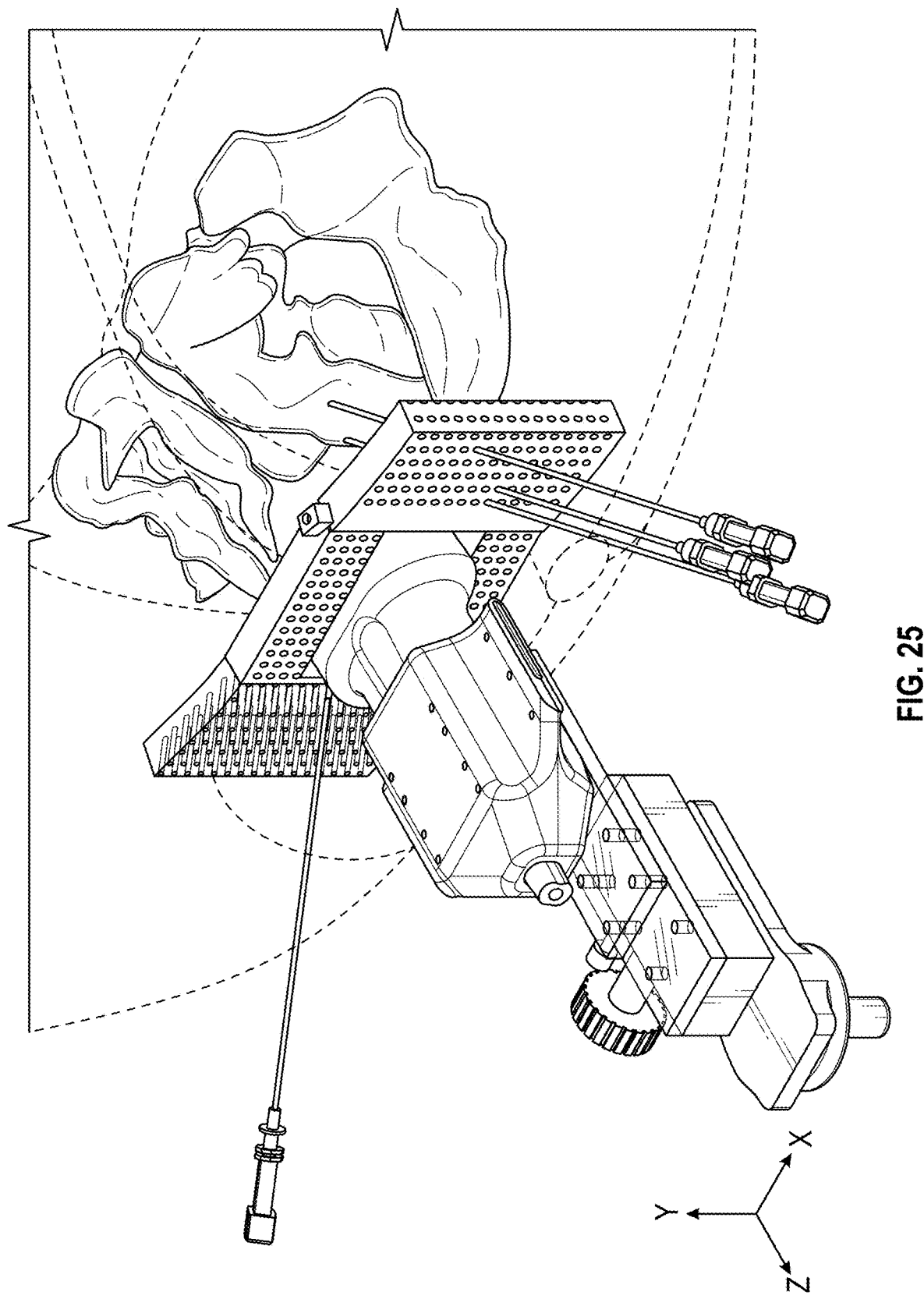
FIG. 25 illustrates another view of the biopsy system shown in FIG. 24.

FIG. 24 shows an enlarged view of the biopsy system shown in FIG. 23A, and FIG. 25 illustrates another view of the biopsy system shown in FIG. 24. By developing 3D solid models as shown in FIGS. 24 and 25, specific patient grids can be designed and constructed to provide biopsy systems that can be used with the transperineal ultrasound imaging techniques described herein to achieve highly accurate needle guidance to tissue areas of interest.

After constructing a suitable model of a grid that achieves the desired trajectories, the patient-specific template grid can be formed using various known techniques, including molding, machining, 3D printing, or some combination of these methods.

Figure 26:
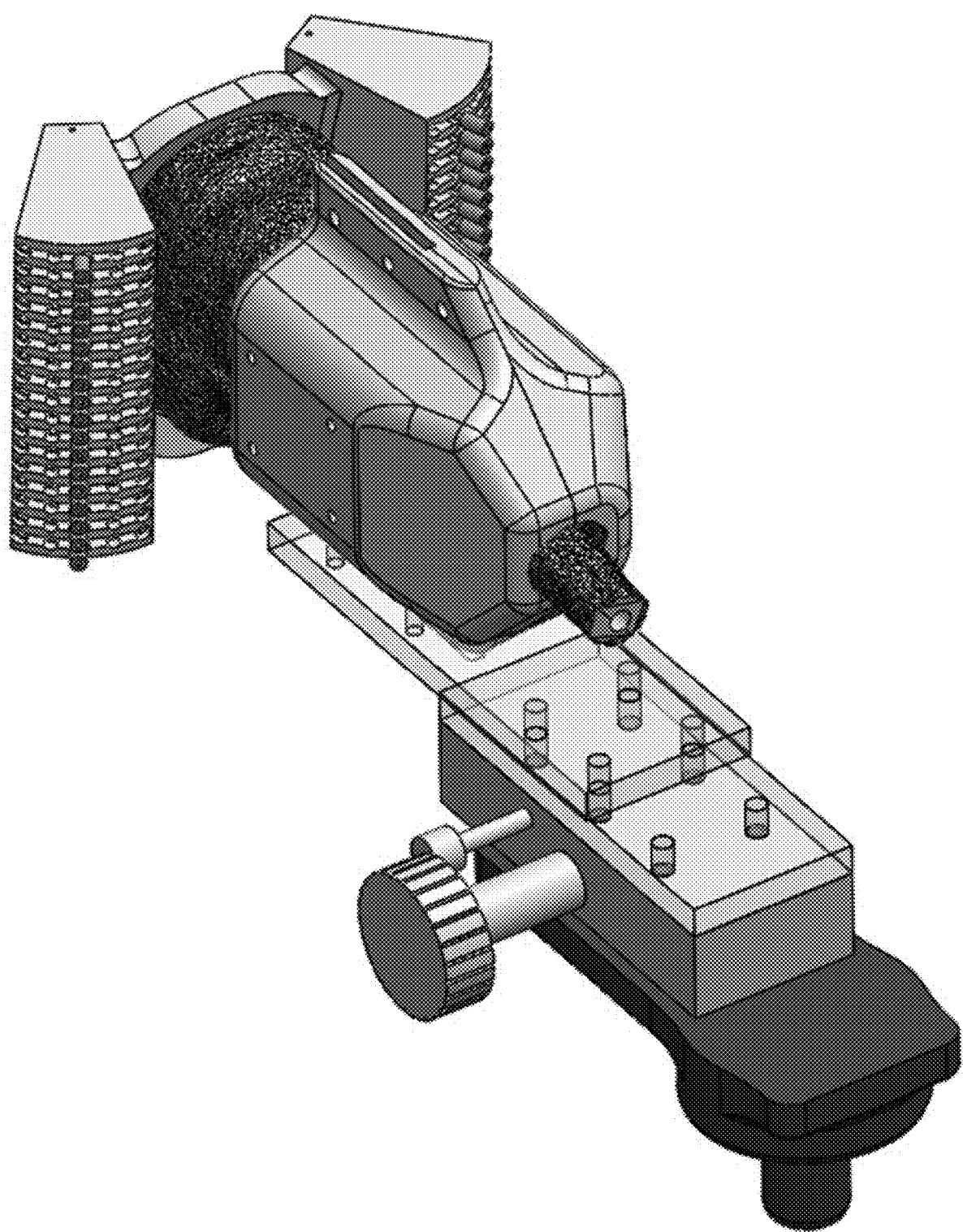
FIG. 26 shows another exemplary transperineal prostate biopsy system that includes a more compact hinged needle guide with 5 pre-defined known angles.
Figure 27:
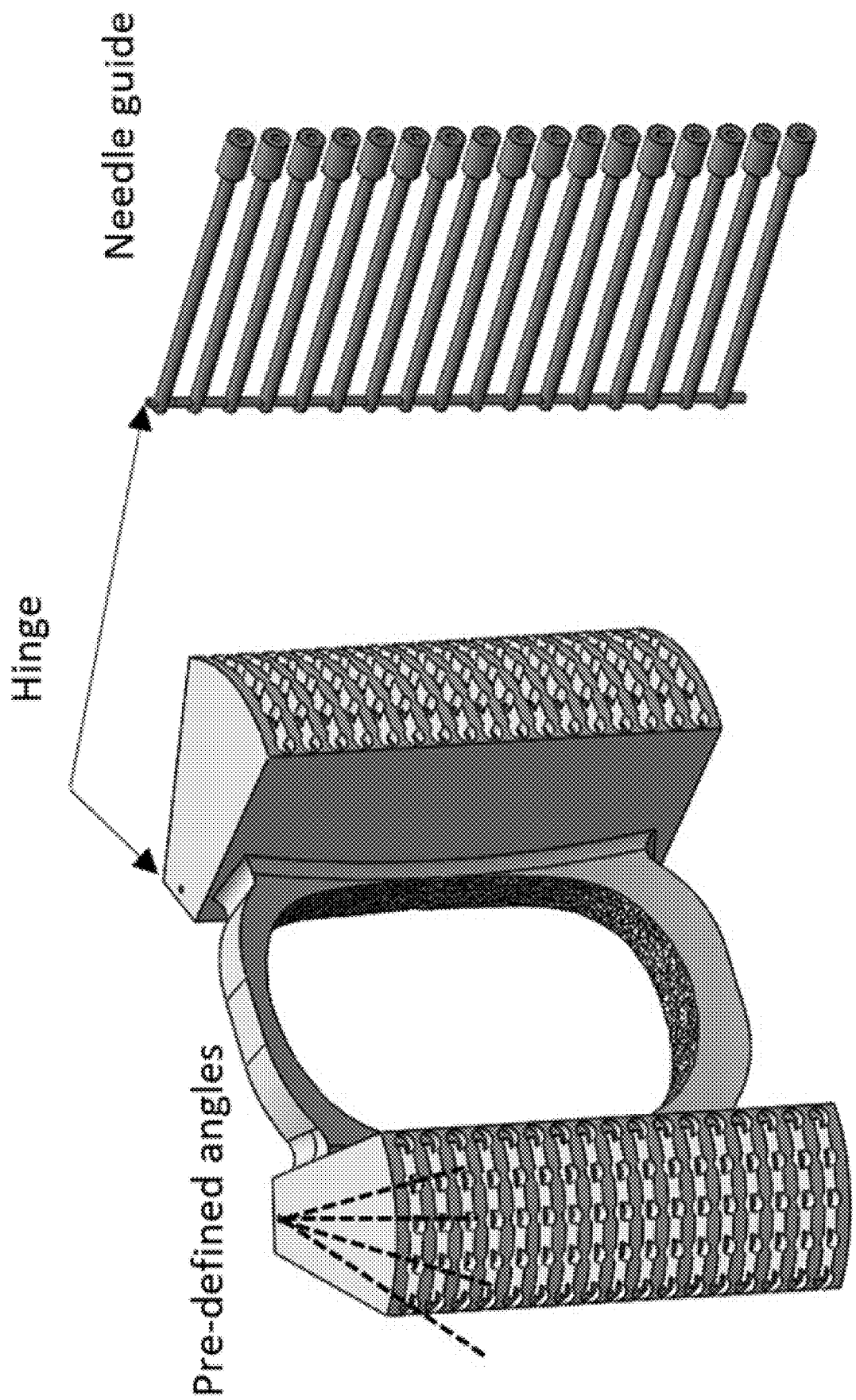
FIG. 27 shows the hinged needle guide of the biopsy system of FIG. 26.
Figure 28:
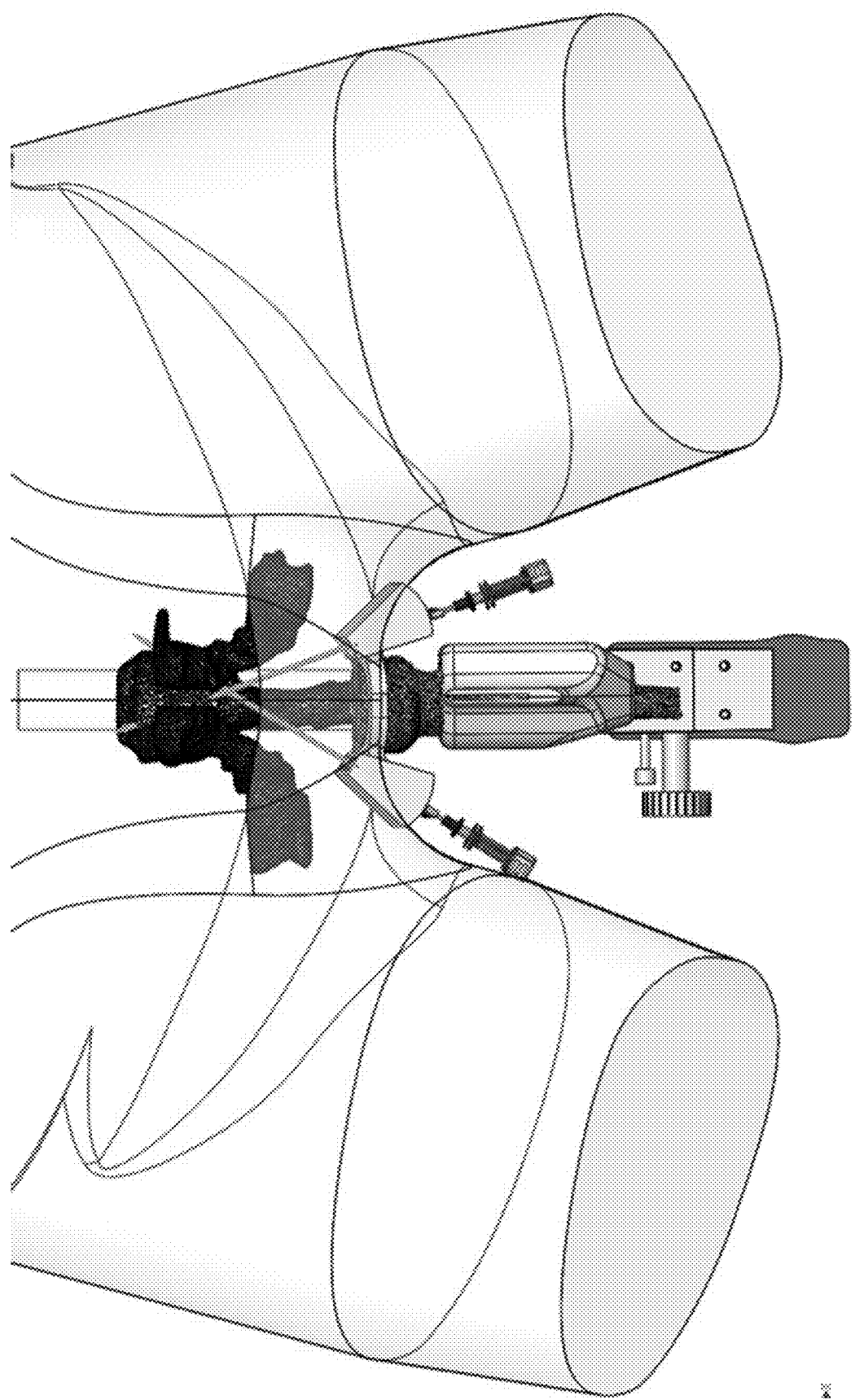
FIGS. 28-29 shows the biopsy system of FIG. 26 in relation to a patient, illustrating its application for taking a prostate biopsy.
Figure 29:
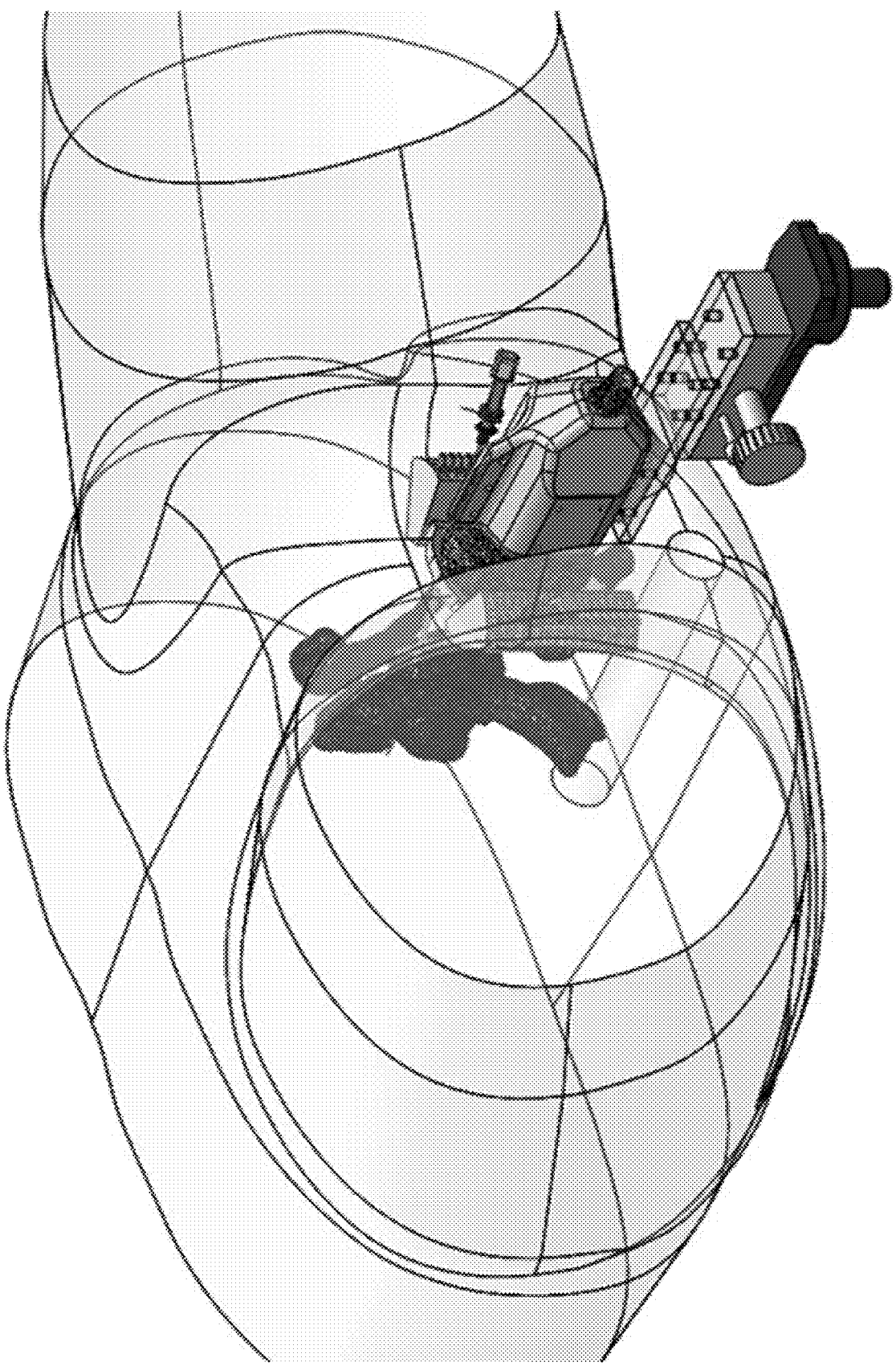

FIG. 26 shows another compact exemplary transperineal prostate biopsy system that includes two hinged needle guides that are coupled to (e.g., snap onto) an ultrasound transducer component (or other imaging component) that is placed along the perineal region of a patient. FIG. 27 shows a needle guide component that includes a ring-shaped mounting portion for attaching to the central imaging component and two hinged needle guides positioned on either lateral side of the mounting portion. In this embodiment, each of the hinged needle guides can be adjusted to 5 different pre-defined angles in relation to the central imaging device. Each pre-defined angle can provide access to a different part of the prostate. The hinged needle guides can comprise a spring load or other biasing mechanism to ensure the needle guides stay in place after each angle adjustment. FIGS. 28-29 shows the biopsy system of FIG. 26 in relation to a patient, illustrating its application for taking a transperineal prostate biopsy.

Figure 30:
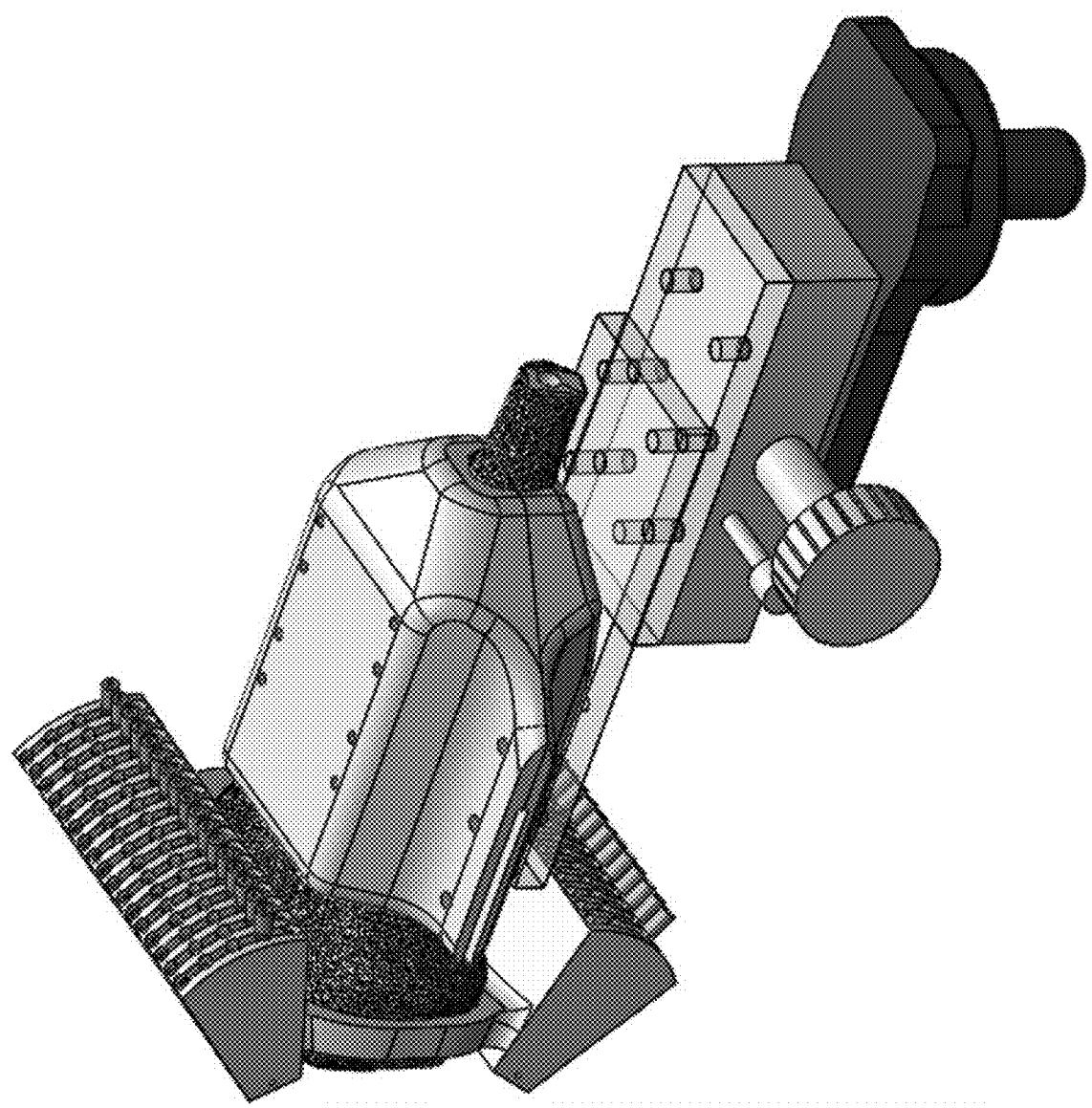
FIG. 30 shows another exemplary transperineal prostate biopsy system that includes a hinged needle guide, wherein the orientation of the needle guide is rotated 90 degrees relative to the embodiment of FIG. 26.
Figure 31:
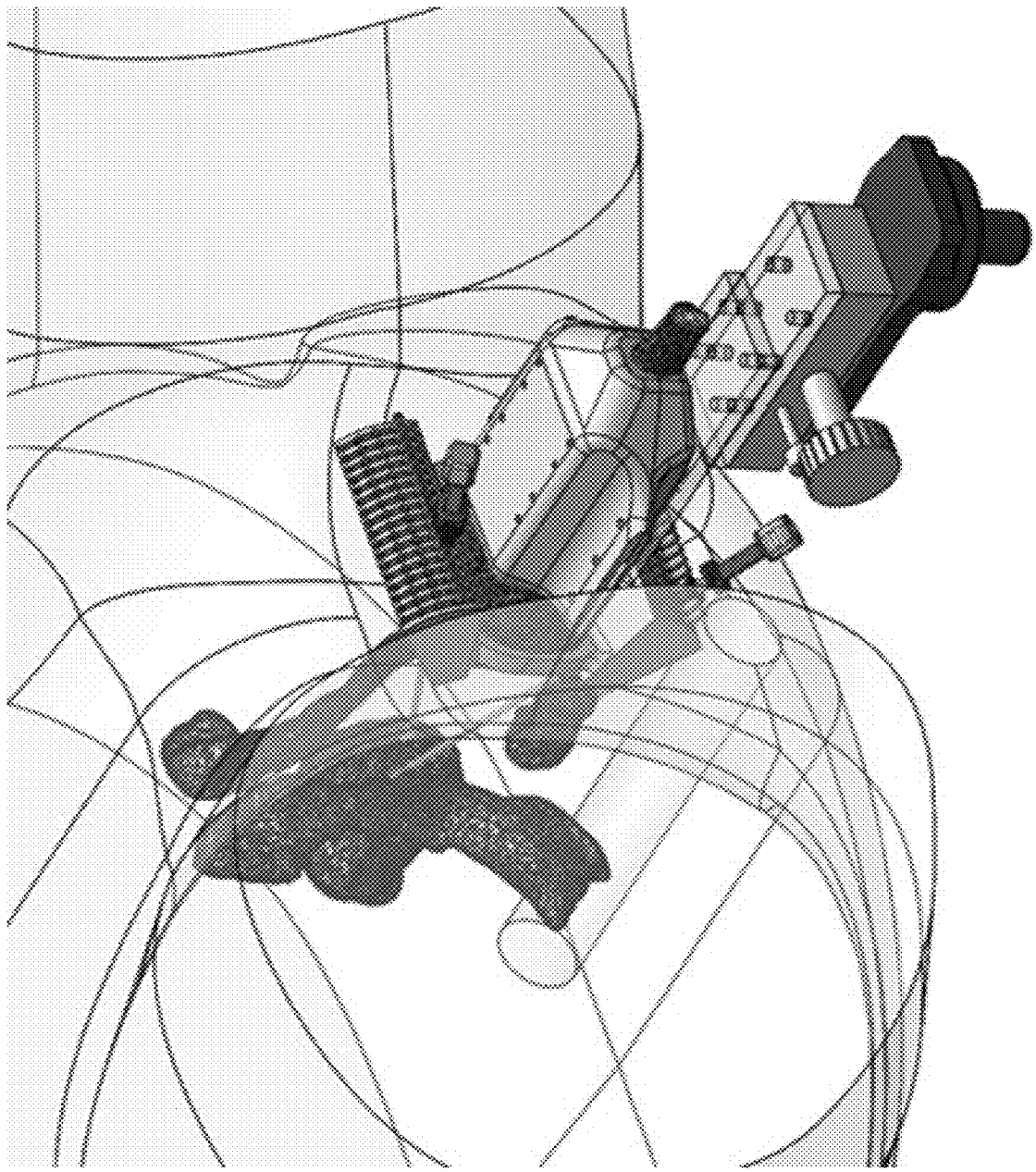
FIG. 31 shows the biopsy system of FIG. 31 in relation to a patient, illustrating its application for taking a prostate biopsy.

FIG. 30 shows another exemplary transperineal prostate biopsy system that includes two hinged needle guides, similar to the embodiment of FIG. 26, but wherein the orientation of the needle guides are rotated 90 degrees relative to the embodiment of FIG. 26. This can provide for additional coverage of the prostate gland, such as to reach areas of the prostate not reachable with the system of FIG. 26. Both the embodiments of FIGS. 26 and 30 can be used in conjunction to provide maximum coverage of the prostate in one biopsy session. FIG. 31 shows the biopsy system of FIG. 30 in relation to a patient, illustrating its application for taking a transperineal prostate biopsy.

Figure 32:
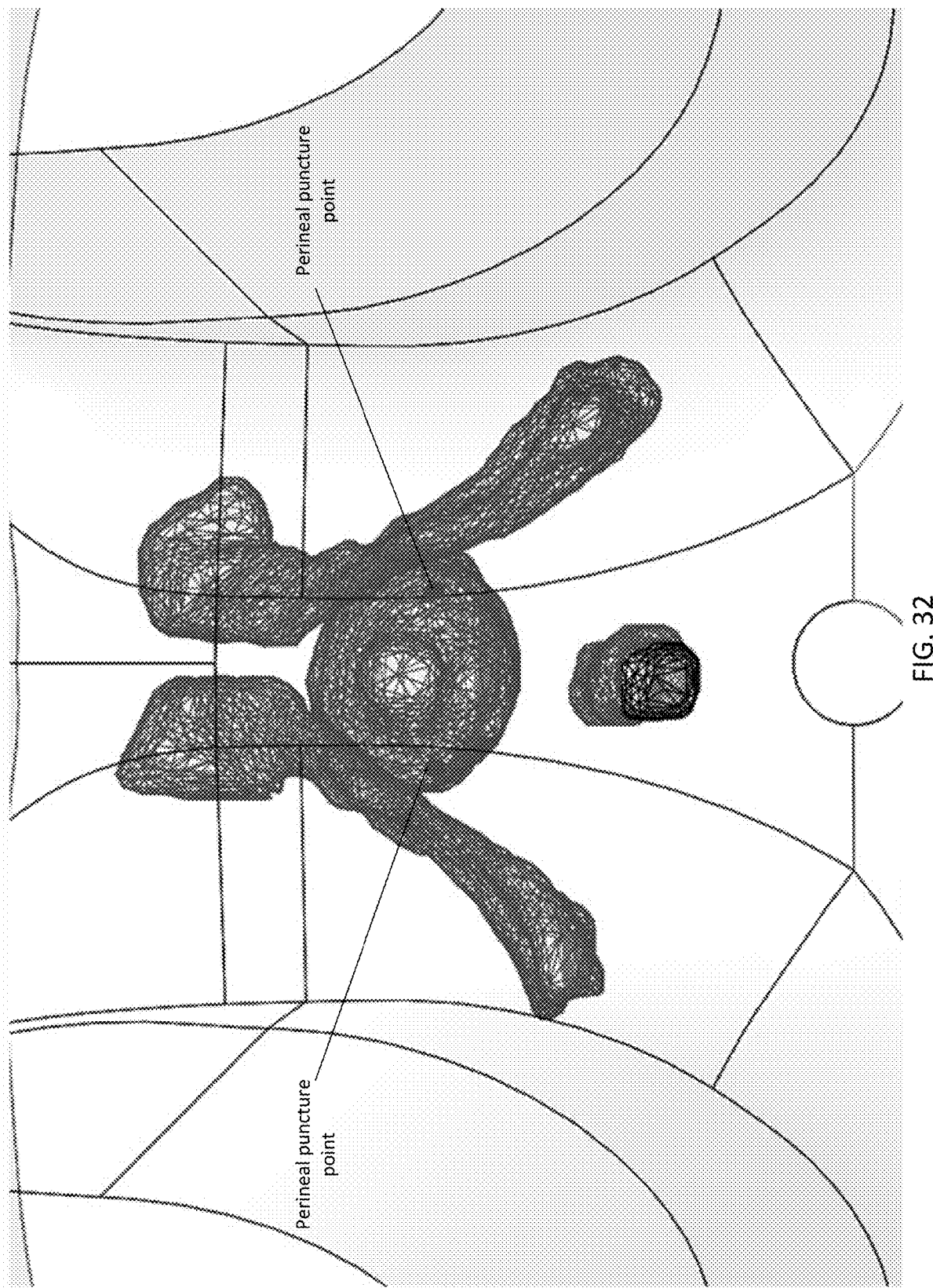
FIG. 32 illustrates a freehand approach to transperineal prostate biopsy with two perineal puncture points used to reach the entire prostate.

FIG. 32 illustrates a relatively different freehand approach to transperineal prostate biopsy with just two perineal puncture points used to reach the entire prostate, which is another preferable approach. By contrast, in a conventional transperineal prostate biopsy approach, an endorectal ultrasound probe is inserted into the rectum and a grid template is placed in front of the perineum for multiple needle punctures. This conventional method includes the following shortcomings: (1) it requires a bulky relatively expensive stepper for positioning of the template and prostate probe; (2) it is not freehand, which is more preferable to urologists; and (3) it requires general anesthesia since there are many punctures through perineum involved. This drawback limits this approach from being an office-based procedure (similar to the conventional transrectal approach).

Some exemplary needle guides attach to a rectal probe and can be used in an approach using just two transperineal entry points. Such a system can be used to reach different parts of the prostate through a single entry point. A short needle guide is inserted through one of the two entry points at a time, once to cover the right half and once to cover the left half of the prostate gland. The anesthetic is injected in the beginning through these entry points. By moving the probe-needle guide assembly, one can maneuver the needle guide such that it reaches different parts of the gland thanks to deformability of the tissues. In other words, one can use only two entry points thus significantly reducing the number of punctures, making the procedure tolerable with local anesthesia and thus being an office-based procedure (and therefore, significantly reducing the costs). The short needle can be in-plane with the ultrasound plane thus providing a guide as to where the needle will end up before insertion of the biopsy needle. However, this system and approach still has the following drawbacks: (1) it requires external tracking device for fusion, which is expected to be required in most future procedures; and (2) it still requires placing the endorectal probe into the patient, which is invasive.

Figure 33:
FIG. 33 show another exemplary transperineal prostate biopsy system that includes two individual needle guides mounted on either side of a central external perineal probe and uses the free-hand, minimally invasive transperineal method described in FIG. 32.
Figure 34:
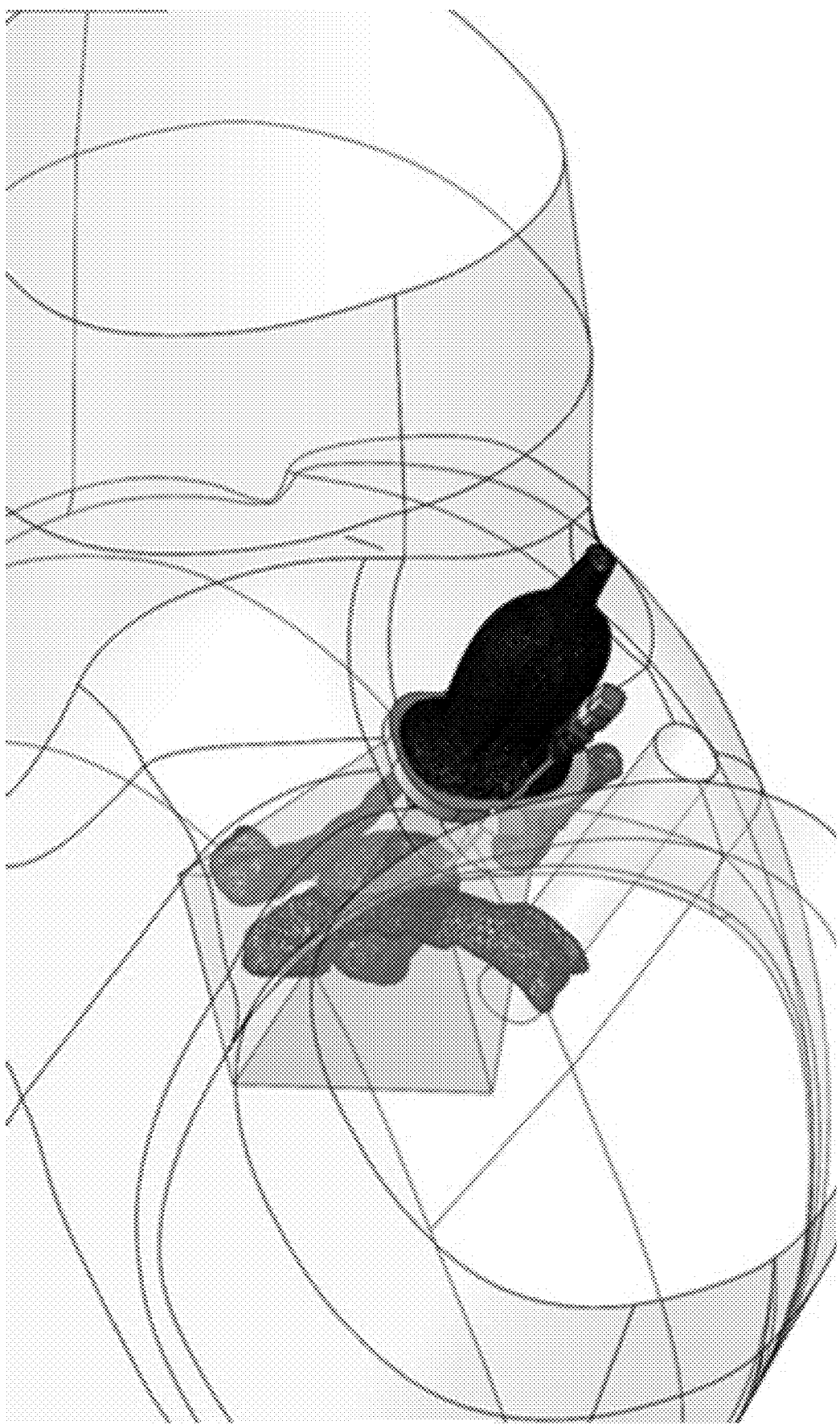
FIG. 34 shows the system of FIG. 33 positioned in relation to a patient, illustrating its application for taking a prostate biopsy.

FIGS. 33-34 show another exemplary transperineal prostate biopsy system that includes two individual needle guides mounted on either side of a central external perineal probe. This embodiment addresses the drawbacks of the system of discussed in the previous paragraph while maintaining the other benefits (e.g., freehand, less infection, no bulky stepper/holder, etc.). FIG. 34 shows the system of FIG. 34 positioned in relation to a patient, illustrating its application for taking a prostate biopsy. FIG. 34 illustrates a 3D imaging field viewable by the probe. In this embodiment, the probe provides the 3D volume in real-time and due to the rigid "snap-in" attachment of the needle guide, the needle trajectory is known. By moving the 3D probe over the perineum, the system can reach different parts of the prostate. Another advantage is that since the probe is moved over the skin, there is a lot less prostate deformation (compared to the approaches with an endorectal probe), which makes the fusion difficult. Also, the "organic" 3D volume can make the 3D ultrasound to 3D MRI registration much easier and smoother and sensorless. It is desirable that the probe be large enough to cover the whole prostate from one hand and small enough to allow some movement over the perineum without losing the sign of the prostate, from the other hand. Exemplary handheld imaging probes that could be adapted for use with the system of FIGS. 33-34 include the X3-1, S51, and X6-1 ultrasound probes available from Philips.

Thus, the systems and methods disclosed herein provide improvements over the state of the art by utilizing non-invasive ultrasound imaging. Unlike TRUS imaging, for example, transperineal ultrasound probes do not enter a body cavity of the patient. This reduces patient discomfort and can decreases the risk of patient injury and/or infection from an invasive procedure. In addition, by using the novel template grid structures disclosed herein, increased trajectory options are available, thereby providing improved access to targeted tissue areas. Also, this system is sensorless both for image fusion and needle placement thus reducing cost of the system and procedure and provide more accurate fusion.

In view of the many possible embodiments to which the principles disclosed herein may be applied, it should be recognized that illustrated embodiments are only examples of the disclosed technology and should not be considered a limitation on the scope of the disclosure. Rather, the scope of the disclosure is at least as broad as the scope of the following claims. We therefore claim all that comes within the scope of these claims.

The invention claimed is:

1. A transperineal prostate biopsy system comprising:
an ultrasound probe support configured to receive an ultrasound probe and be positioned externally of a patient adjacent a perineum of the patient;
one or more template grids having a plurality of apertures extending therethrough to receive and guide a biopsy needle along a transperineal trajectory associated with a respective aperture of the plurality of apertures, the one or more template grids being fixed in position relative to the ultrasound probe support, wherein the one or more template grids comprise at least two laterally-extending grids that extend in at least two lateral directions from the ultrasound probe support; and
a frame coupled to the ultrasound probe support, the frame being movable to position the ultrasound probe adjacent a perineal area of the patient to obtain a transperineal 3D ultrasound image of the patient.

2. The system of claim 1, wherein the one or more template grids comprise an upper template grid that is mounted above the ultrasound probe support, such that when the ultrasound probe is positioned adjacent the perineal area, at least some of the apertures of the upper template grid define needle trajectories that extend over the ultrasound probe.

3. The system of claim 2, wherein the upper template grid is curved and defines a concave side and a convex side, and the upper template grid is mounted above the ultrasound probe support with the concave side facing the patient.

4. The system of claim 2, wherein the upper template grid is pivotably coupled to the ultrasound probe support to allow the upper template grid to move relative to the ultrasound probe support.

5. The system of claim 1, wherein the at least two laterally-extending grids are curved, with respective laterally-extending grids each defining a concave side and a convex side, and the two or more laterally-extending grids being mounted with respective concave sides facing the patient.

6. The system of claim 5, wherein the two or more laterally-extending grids are pivotably coupled to the ultrasound probe support to allow the two or more laterally-extending grids to move relative to the ultrasound probe support.

7. The system of claim 1, wherein the one or more template grids comprise a central grid portion and a pair of laterally-extending grid portions, the central grid portion and pair of laterally-extending grid portions each comprising a plurality of apertures that define needle trajectories.

8. The system of claim 7, wherein the apertures of the central grid portion are generally parallel to each other, and the apertures of respective ones of the pair of laterally-extending grid portions are generally parallel to each other.

9. The system of claim 1, wherein the frame comprises a movable stage that allows the ultrasound probe support to move relative to a portion of the frame; and
wherein the movable stage comprises a linear actuator that permits the movable stage to move towards or away from the patient to facilitate positioning of the ultrasound probe relative to the perineal area of the patient.

10. A method of performing a biopsy of a prostate of a patient, comprising:
coupling an ultrasound probe to an ultrasound probe support, the ultrasound probe support comprising one or more template grids fixed thereto, the ultrasound probe support having a plurality of apertures extending therethrough to receive and guide a biopsy needle along a transperineal trajectory associated with a respective aperture of the plurality of apertures, wherein the one or more template grids comprise at least two laterally-extending grids that extend in at least two lateral directions from the ultrasound probe support;
positioning the ultrasound probe adjacent a perineal area of the patient and external to the patient's rectum, and restricting movement of the ultrasound probe after a desired position is achieved;
acquiring a transperineal 3D ultrasound image of the prostate with the ultrasound probe;
registering the one or more template grids to the ultrasound image;
displaying the ultrasound image and selecting an aperture based on an intersection of a trajectory associated with each aperture with a targeted tissue area of the prostate; and
inserting a biopsy needle into the selected aperture and obtaining a transperineal biopsy sample of the targeted tissue area of the prostate.

11. The method of claim 10, wherein the positioning of the ultrasound probe comprises moving a frame coupled to the ultrasound probe support.

12. The method of claim 11, wherein the act of moving the frame comprises actuating a linear actuator to move a portion of the frame towards the perineal area of the patient.

13. The method of claim 10, wherein the one or more template grids comprise an upper template grid that is mounted above the ultrasound probe support, and the act of inserting the biopsy needle to obtain the biopsy sample comprises passing the biopsy needle over the ultrasound probe as it is positioned adjacent the perineal area of the patient.

14. The method of claim 13, wherein the upper template grid is curved and defines a concave side and a convex side, and the upper template grid is mounted above the ultrasound probe support with the concave side facing the patient.

15. The method of claim 13, further comprising adjusting the position of the upper template guide relative to the ultrasound probe support, wherein the adjustment of the position of the upper template grid is performed by pivoting the upper template grid relative to the ultrasound probe support.

16. The method of claim 10, wherein the at least two laterally-extending grids are curved, with respective laterally-extending grids each defining a concave side and a convex side, and the at least two laterally-extending grids being mounted with respective concave sides facing the patient.

17. The method of claim 16, further comprising adjusting the position of the at least two laterally-extending grids guide relative to the ultrasound probe support, wherein the adjustment of the position of each of the at least two laterally-extending grids is performed by pivoting the respective laterally-extending grid relative to the ultrasound probe support.

18. The method of claim 10, wherein the one or more template grids comprise a central grid portion and a pair of laterally-extending grid portions, the central grid portion and pair of laterally-extending grid portions each comprising a plurality of apertures that define needle trajectories.

19. The method of claim 10, further comprising:
registering a preoperative high-resolution image with the ultrasound image; and
displaying the preoperative high-resolution with the ultrasound image.

* * * * *